United States Patent
Boyall et al.

(10) Patent No.: US 9,499,497 B2
(45) Date of Patent: *Nov. 22, 2016

(54) COMPOUNDS USEFUL AS INHIBITORS OF INDOLEAMINE 2,3-DIOXYGENASE

(71) Applicant: Vertex Pharmaceuticals Incorporated, Boston, MA (US)

(72) Inventors: Dean Boyall, Faringdon (GB); Christopher Davis, Salisbury (GB); James Dodd, Wallingford (GB); Simon Everitt, Beaconsfield (GB); Andrew Miller, Upton Didcot (GB); Peter Weber, Abingdon (GB); James Westcott, Witney (GB); Stephen Young, Oxford (GB); Luca Settimo, Oxford (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 19 days.

This patent is subject to a terminal disclaimer.

(21) Appl. No.: 14/722,413

(22) Filed: May 27, 2015

(65) Prior Publication Data
US 2015/0336903 A1   Nov. 26, 2015

Related U.S. Application Data

(63) Continuation of application No. 14/083,693, filed on Nov. 19, 2013, now Pat. No. 9,073,875.

(60) Provisional application No. 61/757,764, filed on Jan. 29, 2013, provisional application No. 61/728,333, filed on Nov. 20, 2012.

(51) Int. Cl.
| | |
|---|---|
| C07D 249/04 | (2006.01) |
| C07D 401/12 | (2006.01) |
| A61K 31/4192 | (2006.01) |
| A61K 45/06 | (2006.01) |
| A61K 31/4439 | (2006.01) |
| C07D 403/12 | (2006.01) |
| C07D 413/12 | (2006.01) |
| C07D 249/10 | (2006.01) |

(52) U.S. Cl.
CPC ......... *C07D 249/04* (2013.01); *A61K 31/4192* (2013.01); *A61K 31/4439* (2013.01); *A61K 45/06* (2013.01); *C07D 249/10* (2013.01); *C07D 401/12* (2013.01); *C07D 403/12* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 5,059,598 A | 10/1991 | Kanai et al. | |
| 5,326,776 A | 7/1994 | Winn et al. | |
| 6,103,749 A | 8/2000 | Cavalla et al. | |
| 6,248,769 B1 | 6/2001 | Cavalla et al. | |
| 6,451,840 B1 | 9/2002 | Munn et al. | |
| 6,482,416 B2 | 11/2002 | Munn et al. | |
| 8,131,527 B1 | 3/2012 | Saxty et al. | |
| 9,073,875 B2 | 7/2015 | Boyall et al. | |
| 2002/0155104 A1 | 10/2002 | Munn et al. | |
| 2002/0183366 A1 | 12/2002 | Garvey et al. | |
| 2004/0067948 A1 | 4/2004 | Hallett | |
| 2004/0161425 A1 | 8/2004 | Munn et al. | |
| 2004/0234623 A1 | 11/2004 | Munn et al. | |
| 2005/0186289 A1 | 8/2005 | Munn et al. | |
| 2006/0005323 A1 | 1/2006 | Sabelle et al. | |
| 2006/0110371 A1 | 5/2006 | Albert et al. | |

(Continued)

FOREIGN PATENT DOCUMENTS

| CN | 2011097946 | 8/2011 |
|---|---|---|
| DE | 2009134 A1 | 9/1970 |

(Continued)

OTHER PUBLICATIONS

International Search Report and Written Opinion for International Application No. PCT/US2013/070693 mailed Feb. 27, 2014.

(Continued)

*Primary Examiner* — Alicia L Otton
(74) *Attorney, Agent, or Firm* — Wolf, Greenfield & Sacks, P.C.

(57) ABSTRACT

The present invention relates to compounds useful as inhibitors of indoleamine 2,3-dioxygenase (IDO). The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications.

The compounds of this invention have formula I-A:

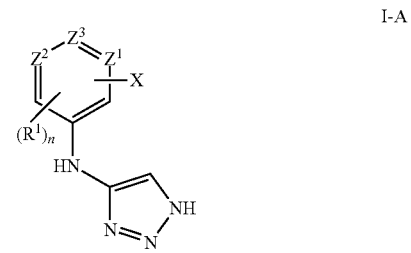

wherein the variables are as defined herein.

29 Claims, No Drawings

(56) References Cited

U.S. PATENT DOCUMENTS

| | | |
|---|---|---|
| 2006/0270733 A1 | 11/2006 | Zisapel et al. |
| 2007/0077234 A1 | 4/2007 | Munn et al. |
| 2007/0099844 A1 | 5/2007 | Prendergast et al. |
| 2008/0125470 A1 | 5/2008 | Combs et al. |
| 2008/0182882 A1 | 7/2008 | Combs et al. |
| 2008/0214546 A1 | 9/2008 | Combs et al. |
| 2009/0053192 A1 | 2/2009 | Millan et al. |
| 2009/0081155 A1 | 3/2009 | Munn et al. |
| 2009/0155311 A1 | 6/2009 | Chen et al. |
| 2010/0022538 A1 | 1/2010 | Boebel et al. |
| 2010/0099684 A1 | 4/2010 | Cook, II et al. |
| 2010/0113523 A1 | 5/2010 | Alberte et al. |
| 2010/0168072 A1 | 7/2010 | Wynne et al. |
| 2010/0180947 A1 | 7/2010 | Smith et al. |
| 2011/0112282 A1 | 5/2011 | Roehrig et al. |
| 2011/0294972 A1 | 12/2011 | Chevalier et al. |
| 2012/0129886 A1 | 5/2012 | Hoekstra et al. |
| 2012/0142750 A1 | 6/2012 | Chen et al. |
| 2012/0149729 A1 | 6/2012 | Hoekstra et al. |
| 2014/0179699 A1 | 6/2014 | Boyall et al. |

FOREIGN PATENT DOCUMENTS

| | | |
|---|---|---|
| DE | 3134842 A1 | 3/1983 |
| EP | 2260846 A1 | 12/2010 |
| JP | 02164863 | 6/1990 |
| WO | WO 90/14338 A1 | 11/1990 |
| WO | WO 93/17681 A1 | 9/1993 |
| WO | WO 93/20066 A1 | 10/1993 |
| WO | WO 95/07908 A1 | 3/1995 |
| WO | WO 98/57951 A1 | 12/1998 |
| WO | WO 99/29310 A2 | 6/1999 |
| WO | WO 99/46244 A1 | 9/1999 |
| WO | WO 00/42029 A1 | 7/2000 |
| WO | WO 01/60816 A1 | 8/2001 |
| WO | WO 02/00651 | 1/2002 |
| WO | WO 02/24645 A1 | 3/2002 |
| WO | WO 03/013523 A1 | 2/2003 |
| WO | WO 03/029225 A1 | 4/2003 |
| WO | WO 03/076437 A1 | 9/2003 |
| WO | WO 03/077921 A1 | 9/2003 |
| WO | WO 03/094920 A1 | 11/2003 |
| WO | WO 2004/014881 A2 | 2/2004 |
| WO | WO 2004/087699 A2 | 10/2004 |
| WO | WO 2004/092146 A2 | 10/2004 |
| WO | WO 2004/093871 A1 | 11/2004 |
| WO | WO 2004/101531 A1 | 11/2004 |
| WO | WO 2006/064375 A2 | 6/2006 |
| WO | WO 2006/069808 A2 | 7/2006 |
| WO | WO 2006/074984 A1 | 7/2006 |
| WO | WO 2006/078621 A2 | 7/2006 |
| WO | WO 2007/002637 A1 | 1/2007 |
| WO | WO 2007/038387 A2 | 4/2007 |
| WO | WO 2007/050405 A2 | 5/2007 |
| WO | WO 2007/051982 A1 | 5/2007 |
| WO | WO 2007/054348 A1 | 5/2007 |
| WO | WO 2007/067875 A2 | 6/2007 |
| WO | WO 2007/081878 A2 | 7/2007 |
| WO | WO 2007/107594 A2 | 9/2007 |
| WO | WO 2008/041088 A2 | 4/2008 |
| WO | WO 2008/070661 A1 | 6/2008 |
| WO | WO 2008/115369 A2 | 9/2008 |
| WO | WO 2008/115973 A2 | 9/2008 |
| WO | WO 2008/135767 A1 | 11/2008 |
| WO | WO 2008/137621 A1 | 11/2008 |
| WO | WO 2008/137622 A2 | 11/2008 |
| WO | WO 2008/149103 A1 | 12/2008 |
| WO | WO 2009/006389 A2 | 1/2009 |
| WO | WO 2009/009442 A2 | 1/2009 |
| WO | WO 2009/047522 A1 | 4/2009 |
| WO | WO 2009/049181 A1 | 4/2009 |
| WO | WO 2009/066060 A2 | 5/2009 |
| WO | WO 2009/067600 A2 | 5/2009 |
| WO | WO 2009/067621 A1 | 5/2009 |
| WO | WO 2009/070579 A2 | 6/2009 |
| WO | WO 2009/081112 A2 | 7/2009 |
| WO | WO 2009/094442 A2 | 7/2009 |
| WO | WO 2009/103650 A1 | 8/2009 |
| WO | WO 2009/104802 A1 | 8/2009 |
| WO | WO 2009/121033 A2 | 10/2009 |
| WO | WO 2009/124252 A2 | 10/2009 |
| WO | WO 2009/127669 A2 | 10/2009 |
| WO | WO 2009/157418 A1 | 12/2009 |
| WO | WO 2010/144338 A1 | 12/2010 |
| WO | WO 2010/144359 A1 | 12/2010 |
| WO | WO 2011/012777 A1 | 2/2011 |
| WO | WO 2011/049274 A1 | 4/2011 |
| WO | WO 2011/056652 A1 | 5/2011 |
| WO | WO 2011/086085 A1 | 7/2011 |
| WO | WO 2011/126903 A2 | 10/2011 |
| WO | WO 2012/064943 A2 | 5/2012 |

OTHER PUBLICATIONS

International Preliminary Report on Patentability for International Application No. PCT/US2013/070693 mailed Jun. 4, 2015.

Baines, K. et al., 5-(Arylamino)-1,2,3-triazolesa nd 5-Amino-1-aryl-1,2,3-triazolefrso from 3-(Cyanomethyl) triazenes; J. Org. Chem. 1981,46,856-859.

Biagi, G. et al., "New 4-(Benzotriazol-1-yl)-1,2,3-Triazole Derivatives", J. Heterocyclic Chem., 33,1847 (1996).

Biagi, G., at al., "Some structural changes on triazolyl-benzotriazoles and triazolyl-benzimidazolones as potential potassium channel activators. III", II Farmaco 56 (2001) 841-849.

Biagi, G., et al., "5-(4'-Substituted-2'-nitroanilino)-1,2,3-triazoles as new potential potassium channel activators. I", Eur. J. Med. Chem. 35 (2000) 715-720.

Biagi, G., et al., "Studies on 1,2,3-triazole derivatives as potential inhibitors of the cyclo-oxygenase", Farmaco Sci 42 (4): 285-97 [1987].

Bojilova. A., et al., "Structure and Specroscopic Characterization of 1- and 2-Hydrazonoy1-1,2,3-triazoles", J. Heterocyclic Chem., 27, 231 (1990).

Buckle, D., et al., "Studies on v-Trizoles. Part 1. Synthesis of 4,9-Dihydro-9-oxo-1H-v-triazolo [4,5-b] quinolines by Cyclization of 5-Arylomino-v-triazole-4-carboxylic Acids with Polyphosphoric Acid.", J. Chem. Research (S), 1980, 308, J. Chem.Research (M), 1980, 3870-3874.

Carboni, S., "Preparation and pharmacological study of some 1,2,3-triazol-1,8-naphthyridine derivatives", Farmaco Sci 33(5) 315-23, (1978).

Gordeev, M., "Synthesis of 5-amino-4-acyl-1,2,3-triazole, 8-azapurine, and 1,2,3-triazolo[4,5- b]pyridine-7-one derivatives using acylketene N,N-acetals and tosyl azide.", Izv Akad Nauk Sssr [Khim], 1990 (6) 1392-1397.

Heep, U., "Synthesis of heterocyclic phosphates ", Justus Liebigs Ann Chem 1973(4): 578-83 [1973].

Huang et al., Structureactivity relationship and enzyme kinetic studies on 4-aryl-1-1,2,3-triazoles as indoleamine 2,3-dioxygenase (IDO) inhibitors. European Journal of Medicinal Chemistry. 2011;46(11):5680-7.

Keshavarz. M., et al., "A simple approach for predicting impact sensitivity of polynitroheteroarenes", Journal of Hazardous Materials 166 (2009) 1115-1119.

Kiselyov. A., et al., "(1,2,3-Triazol-4-yl)benzenamines: Synthesis and activity against VEGF receptors 1 and 2", Bioorganic & Medicinal Chemistry Letters 19 (2009) 1344-1348.

Kuo Wen-Fa et al., "The Syntheses of 4-Arylamino-1,2,3-triazoles and Stable 6-Sydnonyl verdazyls from Sydnone Derivatives and Their Fragments", Journal of the Chinese Chemical Society, 2001, 48, 769-782.

Lieber. E., et al., "Relative Acidities of 5-(Substituted Phenyl)amino-4-phenyl-I,2,3-triazoles", J. Am. Chem. SOC.7,9 , 5962 (1957).

Lieber. E., et al., "Synthesis and Isomerization of Substituted 5-Amino-1,2,3-triazoles", J Org Chem 22(): 654-662 [1957].

(56) References Cited

OTHER PUBLICATIONS

Lieber. E., et al., "The ultra-violet absorption spectra of substituted phenyl amino-1,2,3&triazoles", Spectrochimica Acta, 1958, vol. 10, pp. 260 to 258. Pergamon Press Ltd., London.
Lieber. E., et al., "The Ultraviolet and Infrared Spectra of Vicinal-Triazole Derivatives", Can. J. Chem. vol. 36 (1958) p. 1441-1443.
Livi, O., et al., "[Synthesis and pharmacological activity of 1,2,3-triazole derivatives of naphthalene, quinoline and pyridine]", Farmaco Sci 34(3): 217-28 [1979].
Martin. D., et al., "Cyanic acid esters. VII. Cyanic acid esters as dienophiles in 1,3-cycloadditions", Chem Ber 99(1) : 317-27 1966.
Quilico. A., et al., "The structure of the reaction products of nitric acid on acetylene. VI. Acetylene", Gazz Chim Ital 61 ( ) : 759-72 1931.
Qvortrup. K., et al., "A photolabile linker for the solid-phase synthesis of 4-substituted", Chem. Commun., 2011, 47, 3278-3280.
Rohrig. U., et al., "Rational Design of 4-Aryl-1,2,3-Triazoles for Indoleamine 2,3-Dioxygenase 1 Inhibition", J Med Chem. Jun. 14, 2012;55(11):5270-90. doi: 10.1021/jm300260v. Epub May 22, 2012.
Settimo et al., "1,2,3-triazole derivatives of arylalkanoic acids", Farmaco Sci 34(5) : 371-82, 1979.
Shaw. J., et al., "The Preparation of 2,6-Diaminopyrazine, 2,6-Diazidopyrazine and Some of Their Derivatives", J. Heterocyclic Chem., 17, 11 (1980).
Tanaka. Y., et al., "Synthesis and Nucleophilic Properties of 4-Aryl-5-triphenylphosphonium-1,2,3-triazole Ylides or 4-Aryl-1,2,3-triazol-5-yltriphenylphosphoranes", J. Org. Chem., vol. 38, No. 16, 1973.
Tome. A.C., "Product Class 13: 1,2,3-Triazoles", A. C. Tome, Section 13.13, Science of Synthesis, 2004 Georg Thieme Verlag KG.
Wamhoff. H., et al., "Heterocyclic B-Enamino Esters 43—Easy C NMR Distinction between Aryl-Substituted Dimroth Isomers of the 1,2,3-Triazole Series", Magnetic Resonance in Chemistry, vol. 24, 809-811 (1986).
Wang. H., et al., "Copper-Catalyzed Synthesis of 4-Aryl-1H-1,2,3-triazoles from 1,1-Dibromoalkenes and Sodium Azide", Eur. J. Org. Chem. 2012, 424-428.
Yan. W., et al., "Synthesis of allene triazole through iron catalyzed regioselective addition to propargyl alcohols", Chem. Commun., 2012, 48, 3521-3523.

COMPOUNDS USEFUL AS INHIBITORS OF INDOLEAMINE 2,3-DIOXYGENASE

CROSS-REFERENCE TO RELATED APPLICATIONS

The present application is a continuation of U.S. Non-Provisional application Ser. No. 14/083,693, filed Nov. 19, 2013, claims the benefit of under 35 U.S.C. §119 U.S. Provisional Application No. 61/728,333, filed Nov. 20, 2012, as well as U.S. Provisional Application No. 61/757,764, filed Jan. 29, 2013.

BACKGROUND OF THE INVENTION

Tryptophan (Trp) is an essential amino acid necessary for the biosynthesis of proteins, niacin, and the neurotransmitter 5-hydroxytryptamine (serotonin). The heme-dependent oxygenase indoleamine 2,3-dioxygenase (also named INDO or IDO) is responsible for the extra-hepatic conversion of Trp to N-formyl-kynurenine as a rate-limiting first step of Trp metabolism. N-formyl-kynurenine is a precursor of a variety of bioactive molecules called kynurenines that have immunomodulatory properties (Schwarcz et al., Nat Rev Neurosci. 2012; 13(7):465-77).

IDO was initially described as part of the mammalian defense mechanism against parasite infection. Depletion of Trp can lead to growth arrest of intracellular pathogens such as *Toxoplasma gondii* or *Chlamydia trachomatis* (MacKenzie et al., Curr Drug Metab. 2007; 8(3):237-44). More recently, it has become apparent that IDO is an inducible enzyme that has a primary role in immune cell modulation. The reduction of Trp levels and increase in the pool of kynurenines cause inhibition of effector immune cells and promote adaptive immune suppression through induction and maintenance of regulatory T cells (Tregs; Munn, Front Biosci. 2012; 4:734-45).

Increased turnover of Trp to kynurenines by IDO has been observed in a number of disorders linked to activation of the immune system, e.g. infection, malignancy, autoimmune diseases, trauma and AIDS (Johnson and Munn, Immunol Invest 2012; 41(6-7): 765-97). Additional studies in these indications have shown that induction of IDO results in suppression of T-cell responses and promotion of tolerance. In cancer, for example, a large body of evidence suggests that IDO upregulation serves as a mechanism in tumour cells to escape immune surveillance. IDO is expressed widely in solid tumours (Uyttenhove et al., Nat Med. 2003; 10:1269-74) and has been observed in both primary and metastatic cancer cells. IDO is induced in tumours by proinflammatory cytokines, including type I and type II interferons that are produced by infiltrating lymphocytes (Tnani and Bayard, Biochim Biophys Acta. 1999; 1451(1):59-72; Mellor and Munn, Nat Rev Immunol 2004; 4(10):762-74; Munn, Front Biosci. 2012; 4:734-45) and TGF-Beta (Pallotta et al., Nat Immunol. 2011; 12(9):870-8). Certain oncogenic mutations can also lead to increased IDO expression, e.g., loss of the tumour suppressor Bin1 (Muller et al, Nat Med. 2005; 11(3):312-9) or activating mutations in KIT (Balachandran et al., Nat Med. 2011; 17(9): 1094-1100). IDO expression has been correlated with immune anergy in some tumours (e.g. Ino et al., Clin Cancer Res. 2008 Apr. 15; 14(8):2310-7; Brandacher et al., Clin. Cancer Res. 2006 Feb. 15; 12(4): 1144-51), and a recent report has shown that reduction of IDO expression in human gastrointestinal tumours goes along with an increased infiltration of tumours by effector T cells (Balachandran et al., Nat Med. 2011; 17(9): 1094-1100).

A significant amount of preclinical data has been published that further validates the role of IDO in the anti-tumour immune response. For example, forced IDO induction in cancer cells was shown to confer a survival advantage (Uyttenhove et al., Nat Med. 2003; 10:1269-74). Other in vivo studies showed that IDO inhibitors cause lymphocyte dependent reduction in tumour growth by lowering kynurenine levels (Liu et al., Blood. 2010; 115(17):3520-30). Preclinical studies also highlighted the scope for IDO inhibitors to work synergistically in combination with agents that promote tumour antigenicity like irradiation, chemotherapy or vaccines (Koblish et al., Mol Cancer Ther. 2010; 9(2): 489-98, Hou et al., Cancer Res. 2007; 67(2):792-801; Sharma et al., Blood. 2009; 113(24):6102-11).

In addition to creating an immune suppressive environment in tumours, IDO has also been implicated in inducing tolerance in lymph nodes, a phenomenon that seems to further contribute to immune evasion in cancer (Munn, Curr Opin Immunol. 2006; 18(2):220-5). IDO expression has been reported in antigen presenting cells, e.g. dendritic cells (DCs), which migrate to lymph nodes and induce anergy. IDO-positive DCs in tumour draining lymph nodes (TDLNs) of cancer-bearing mice have been shown to prevent the conversion of Tregs to inflammatory T-helper-17 (Th17)-like cells (Sharma et al., Blood. 2009; 113(24):6102-11), thereby blocking T-cell activation. Conversion of Tregs into proinflammatory Th17-like cells occurred when IDO activity was blocked with the IDO inhibitor 1-MT. IDO activity in TDLNs therefore provides an important aspect of the rationale for its inhibition as a cancer therapy.

IDO-mediated formation of kynurenines has recently also been implicated in mechanisms beyond the regulation of the immune system. For example, numerous studies since the 1970s have demonstrated that kynurenines can influence brain function. Kynurenine pathway metabolites are now seen as potential causative factors in several devastating brain diseases. Fluctuations in the level of kynurenine pathway metabolites can lead to the deterioration of physiological processes and the emergence of pathological states, e.g., neurodegenerative diseases, schizophrenia and depression (Schwarcz et al., Nat Rev Neurosci. 2012; 13(7):465-77). Furthermore, IDO-mediated kynurenine production in blood vessels has been linked to vasodilation and shock in inflammation and sepsis (Wang et al., Nat. Med 2010; 16(3):279-85). IDO expression has been observed in resistance vessels in human sepsis, and IDO activity correlates with hypotension in human septic shock (Changsirivathanathamrong et al., Crit Care Med. 2011; 39(12):2678-830). In clinical studies with sepsis and bacteremia patients, IDO-mediated tryptophan catabolism has been associated with dysregulated immune responses and impaired microvascular reactivity (Darcy et al., PLoS One. 2011; 6(6):e21185), as well as survival and disease severity (Huttunen et al., Shock. 2010; 33(2):149-54). Similarly, in community acquired pneumonia patients, IDO activity correlates with negative outcome and disease progression, including sepsis severity (Suzuki et al., J Infect. 2011; 63(3):215-22). There is therefore a strong rationale for inhibition of IDO activity in bacterial infections and sepsis.

Taken together, there is a need for the development of potent and selective IDO inhibitors, either as single agents or combination therapies, to modulate the kynurenine pathway and maintain physiological tryptophan levels in the body to more effectively combat diseases and conditions resulting from the harmful products of the kynurenine pathway, abnormal deviations in the levels of kynurenine pathway metabolites, or decreases in tryptophan levels. Such inhibitors counteract immune suppression, vasodilation and neurotoxicity that have been linked to the activity and expression of the IDO enzyme.

SUMMARY OF THE INVENTION

This invention relates to compounds and compositions useful as indoleamine 2,3-dioxygenase (IDO) inhibitors. The invention also relates to pharmaceutically acceptable compositions comprising the compounds of this invention; processes for preparing the compounds of this invention; intermediates for the preparation of the compounds of this invention; methods of using the compounds in in vitro applications, such as the study of IDO1 in biological and pathological phenomena; and the study of intracellular signal transduction.

Moreover, these compounds and pharmaceutically acceptable compositions thereof are very potent IDO inhibitors and are useful for treating or preventing a variety of diseases, disorders or conditions including, but not limited to, cancer and sepsis.

DETAILED DESCRIPTION OF THE INVENTION

This invention describes compounds of Formula I-A:

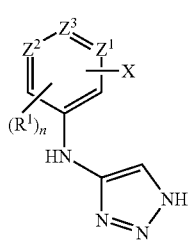

I-A or a pharmaceutically acceptable salt or prodrug thereof, wherein:
n is 0-4;
X is halo;
$Z^1$, $Z^2$, and $Z^3$ are CH or N;
$R^1$ is independently selected from halo; —CN; $Q^X$; or a $C_{1-10}$aliphatic chain wherein up to four methylene units of the aliphatic chain are optionally replaced with —O—, —NR—, —S—, —C(O)—, S(O)—, or —S(O)$_2$—; $R^1$ is optionally substituted with 0-5 $J^1$ groups;
$Q^X$ is a 3-7 membered monocyclic fully saturated, partially unsaturated, or aromatic ring containing 0-3 heteroatoms independently selected from nitrogen, oxygen, or sulfur;
$J^1$ is independently selected from halo; —CN; $Q^Y$; or a $C_{1-6}$aliphatic chain wherein up to three methylene units of the aliphatic chain are optionally replaced with —O—, —NR—, —S—, —C(O)—, —S(O)—, or —S(O)$_2$—; $J^1$ is optionally substituted with 0-5 $J^2$ groups; or
two occurrences of $J^1$ on the same atom, together with the atom to which they are attached, form a 3-6 membered non-aromatic monocyclic ring; the ring formed by two occurrences of $J^1$ on the same atom is optionally substituted with 0-3 $J^{2A}$ groups; or
two occurrences of $J^1$, together with $Q^X$, form a bridged ring system;

$Q^Y$ is independently selected from a 3-7 membered monocyclic fully saturated, partially unsaturated, or aromatic ring containing 0-3 heteroatoms independently selected from nitrogen, oxygen, or sulfur; or an 8-12 membered bicyclic fully saturated, partially unsaturated, or aromatic ring containing 0-5 heteroatoms independently selected from nitrogen, oxygen, or sulfur;
$J^2$ is independently selected from halo; =O; —CN; a 3-6 membered aromatic or non-aromatic ring containing 0-3 heteroatoms selected from oxygen, nitrogen, or sulfur; or $C_{1-4}$aliphatic chain wherein up to two methylene units of the aliphatic chain are optionally replaced with —O—, —NR—, —S—, —C(O)—, S(O)—, or —S(O)$_2$—; $J^2$ is optionally substituted with 0-5 $J^3$ groups; or
two occurrences of $J^2$, together with the atom or atoms to which they are attached, form a 3-6 membered aromatic or non-aromatic monocyclic ring; the ring formed by two occurrences of $J^2$ is optionally substituted with 0-3 $J^{3A}$ groups; or
two occurrences of $J^2$, together with $Q^Y$, form a bridged ring system;
$J^{2A}$ is independently selected from halo or a $C_{1-4}$aliphatic chain wherein up to two methylene units of the aliphatic chain are optionally replaced with —O—, —NR—, —S—, —S(O)—, —S(O)$_2$, or —C(O);
$J^3$ and $J^{3A}$ are independently selected from halo or $C_{1-4}$alkyl; and
R is independently selected from H or $C_{1-6}$aliphatic.

For purposes of this application, it will be understood that when two occurrences of $J^1$, together with $Q^X$, form a bridged ring system, the two occurrences of $J^1$ are attached to separate atoms of $Q^X$. Moreover, when two occurrences of $J^2$, together with $Q^Y$, form a bridged ring system, the two occurrence of $J^2$ are attached to separate atoms of $Q^Y$.

In some embodiments, the present invention is a compound of formula I-A, wherein $Z^1$, $Z^2$, and $Z^3$ are CH. In other embodiments, the present invention is a compound of formula I-A, wherein $Z^1$ and $Z^2$ are CH and $Z^3$ is nitrogen. In another embodiment, the present invention is a compound of formula I-A, wherein $Z^1$ and $Z^2$ are nitrogen and $Z^3$ is CH. In yet another embodiment, the present invention is a compound of formula I-A, wherein $Z^1$ and $Z^3$ are CH and $Z^2$ is nitrogen. It will be understood that throughout the application $Z^1$, $Z^2$, or $Z^3$ can be substituted with $R^1$ when $Z^1$, $Z^2$, or $Z^3$ is CH.

In another embodiment, the present invention is a compound of formula I-A, wherein X is selected from bromo or chloro. In other embodiments, the present invention is a compound of formula I-A, wherein X is bromo. In yet another embodiment, the present invention is a compound of formula I-A, wherein X is chloro.

In some embodiments, the present invention is a compound of formula I-A, wherein n is 0.

In another embodiment, the present invention is a compound of formula I-A, wherein $R^1$ is independently selected from halo, —CN, or a $C_{1-8}$aliphatic chain wherein up to four methylene units of the aliphatic chain are optionally replaced with —O—, —NR—, —C(O)—, or —S(O)$_2$—.

In some embodiments, the present invention is a compound of formula I-A, wherein $R^1$ is a $C_{1-6}$aliphatic chain wherein up to three methylene units of the aliphatic chain are optionally replaced with —O—, —NR—, —C(O)—, or S(O)$_2$. In another embodiment, the present invention is a compound of formula I-A, wherein $R^1$ is independently selected from $C_{1-6}$alkyl, —($C_{1-4}$alkyl)O($C_{1-4}$alkyl), —NHSO$_2$($C_{1-4}$alkyl), —($C_{1-4}$alkyl)NHC(O)($C_{1-4}$alkyl), —CO$_2$($C_{1-4}$alkyl), —($C_{1-4}$alkyl)NHSO$_2$($C_{1-4}$alkyl), —(C$_{1-4}$alkyl)SO$_2$NH(C$_{1-4}$alkyl), —C(O)NH(C$_{1-4}$alkyl), —C(O)NH, —O(C$_{1-4}$alkyl), —(C$_{1-4}$alkyl)NHCO$_2$(C$_{1-4}$alkyl), —SO$_2$(C$_{1-4}$alkyl), —(C$_{1-4}$alkyl)CH(O), —(C$_{1-4}$alkyl)NH$_2$, —(C$_{1-4}$alkyl)OH, —(C$_{1-4}$alkyl)C(O)OH, or —C(O)NH$_2$.

In yet another embodiment, the present invention is a compound of formula I-A, wherein R$^1$ is independently selected from C$_{1-6}$alkyl, —(C$_{1-4}$alkyl)O(C$_{1-4}$alkyl), —(C$_{1-4}$alkyl)SO$_2$NH(C$_{1-4}$alkyl), —(C$_{1-4}$alkyl)NHC(O)(C$_{1-4}$alkyl), —(C$_{1-4}$alkyl)NHSO$_2$(C$_{1-4}$alkyl), —(C$_{1-4}$alkyl)NHCO$_2$(C$_{1-4}$alkyl), or —O(C$_{1-4}$alkyl). In some embodiments, the present invention is a compound of formula I-A, wherein R$^1$ is independently selected from C$_{1-6}$alkyl, —O(C$_{1-4}$alkyl), or —(C$_{1-4}$alkyl)O(C$_{1-4}$alkyl).

In another embodiment, the present invention is a compound of formula I-A, wherein R$^1$ is —CN.

In other embodiments, the present invention is a compound of formula I-A, wherein R$^1$ is halo.

In some embodiments, the present invention is a compound of formula I-A, wherein J$^1$ is independently selected from halo, a C$_{1-6}$aliphatic, or Q$^Y$.

In one embodiment, the present invention is a compound of formula I-A, wherein J$^1$ is halo. In other embodiments, J$^1$ is fluoro.

In some embodiments, the present invention is a compound of formula I-A, wherein J$_1$ is a C$_{1-6}$aliphatic.

In yet another embodiment, the present invention is a compound of formula I-A, wherein J$^1$ is Q$^Y$. In some embodiments, the present invention is a compound of formula I-A, wherein Q$^Y$ is independently selected from a 5-6 membered aryl or heteroaryl, a 3-7 membered cycloaliphatic, or a 3-7 membered heterocyclyl; the heteroaryl and heterocyclyl having 1-3 heteroatoms selected from oxygen, nitrogen, or sulfur.

In another embodiment, the present invention is a compound of formula I-A, wherein Q$^Y$ is independently selected from a 3-7 membered cycloaliphatic or a 3-7 membered heterocyclyl having 1-2 heteroatoms independently selected from oxygen, nitrogen, or sulfur. In some embodiments, the present invention is a compound of formula I-A, wherein Q$^Y$ is independently selected from cyclopropyl, cyclobutyl, cyclopentyl, cyclohexyl, cycloheptyl, piperidinyl, azepanyl, pyrrolidinyl, piperazinyl, morpholinyl, thiomorpholinyl, pyrazolidinyl, isoxazolidinyl, thiazolidinyl, imidazolidinyl, 1,4-diazepanyl, 1,4-oxazepanyl, 1,4-thiazepanyl, 1,3-oxazinanyl, or 1,3-thiazinanyl. In other embodiments, the present invention is a compound of formula I-A, wherein Q$^Y$ is independently selected from cyclobutyl, piperazinyl, or morpholinyl.

In some embodiments, the present invention is a compound of formula I-A, wherein Q$^Y$ is a 5-6 membered aryl or heteroaryl. In other embodiments, the present invention is a compound of formula I-A, wherein J$^1$ is independently selected from phenyl, pyrrolyl, pyridinyl, isoxazolyl, pyrimidinyl, imidazolyl, pyrazinyl, or pyrazolyl. In one embodiment, the present invention is a compound of formula I-A, wherein Q$^Y$ is phenyl.

In yet another embodiment, the present invention is a compound of formula I-A, wherein J$^2$ is halo.

In other embodiments, the present invention is a compound of formula I-A, wherein J$^2$ is a 3-6 membered aromatic or non-aromatic monocyclic ring having 1-3 heteroatoms selected from oxygen, nitrogen, or sulfur. In another embodiment, the present invention is a compound of formula I-A, wherein J$^2$ is independently selected from cyclopopyl, cyclobutyl, or phenyl.

In some embodiments, the present invention is a compound of formula I-A, wherein J$^2$ is independently selected from a C$_{1-4}$aliphatic chain wherein up to two methylene units of the aliphatic chain are optionally replaced with —O—, —NR—, —S—, —C(O)—, —S(O)— or S(O)$_2$. In another aspect, the present invention is a compound of formula I-A, wherein J$^2$ is independently selected from —C(O)OH or —C$_{1-4}$alkyl.

In another example, the invention describes compounds of formula I-A having the formula:

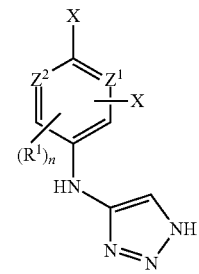

I-B or a pharmaceutically acceptable salt or prodrug thereof, wherein

X is bromo or chloro.

In some embodiments, Z$^1$ and Z$^2$ of formula I-B are nitrogen. In other embodiments, only one of Z$^1$ or Z$^2$ of formula I-B is nitrogen. In yet another embodiment, Z$^1$ and Z$^2$ of formula I-B are CH.

In another example, X of formula I-B is chloro.

In yet another aspect, n of formula I-B is 0.

In another embodiment, R$^1$ of formula I-B is independently selected from halo, —CN, or a C$_{1-8}$aliphatic chain wherein up to four methylene units of the aliphatic chain are optionally replaced with —O—, —NR—, —C(O)—, or —S(O)$_2$—.

In yet another example, R$^1$ of formula I-B is a C$_{1-6}$aliphatic chain wherein up to four methylene units of the aliphatic chain are optionally replaced with —O—, —NR—, —C(O)—, or —S(O)$_2$—. In some embodiments, R$^1$ of formula I-B is independently selected from C$_{1-6}$alkyl, —(C$_{1-4}$alkyl)O(C$_{1-4}$alkyl), —(C$_{1-4}$alkyl)OH, —O(C$_{1-4}$alkyl), —(C$_{1-4}$alkyl)SO$_2$NH(C$_{1-4}$alkyl), —(C$_{1-4}$alkyl)NHC(O)(C$_{1-4}$alkyl), —(C$_{1-4}$alkyl)NHSO$_2$(C$_{1-4}$alkyl), —(C$_{1-4}$alkyl)NHCO$_2$(C$_{1-4}$alkyl), or —(C$_{1-4}$alkyl)C(O)OH. In another embodiment, R$^1$ of formula I-B is independently selected from C$_{1-6}$alkyl, —O(C$_{1-4}$alkyl), or —(C$_{1-4}$alkyl)O(C$_{1-4}$alkyl).

In another aspect, R$^1$ of formula I-B is —CN.

In another example, R$^1$ of formula I-B is halo.

In some embodiments, J$^1$ of formula I-B is independently selected from halo, a C$_{1-6}$aliphatic, or a 3-7 membered aromatic or non-aromatic ring containing 0-4 heteroatoms independently selected from nitrogen, oxygen, or sulfur.

In one embodiment, J$_1$ of formula I-B is C$_{1-6}$aliphatic. In another embodiment, J$_1$ of formula I-B is C$_{1-4}$alkyl.

In other embodiments, J$^1$ of formula I-B is a 3-6 membered cycloaliphatic or a 3-6 membered heterocyclyl having 1-2 heteroatoms selected from oxygen, nitrogen, or sulfur. In another embodiment, J$^1$ of formula I-B is independently selected from cyclopropyl, cyclobutyl, cyclopentyl, cyclohexyl, piperidinyl, pyrrolidinyl, piperazinyl, morpholinyl, or thiomorpholinyl. In yet another embodiment, J$^1$ of formula I-B is independently selected from cyclobutyl, piperazinyl, or morpholinyl.

In another example, the compounds of this invention are represented in Table 1. It will be appreciated by those skilled in the art that the compounds of the present invention may be represented in varying tautomeric forms.
TABLE 1
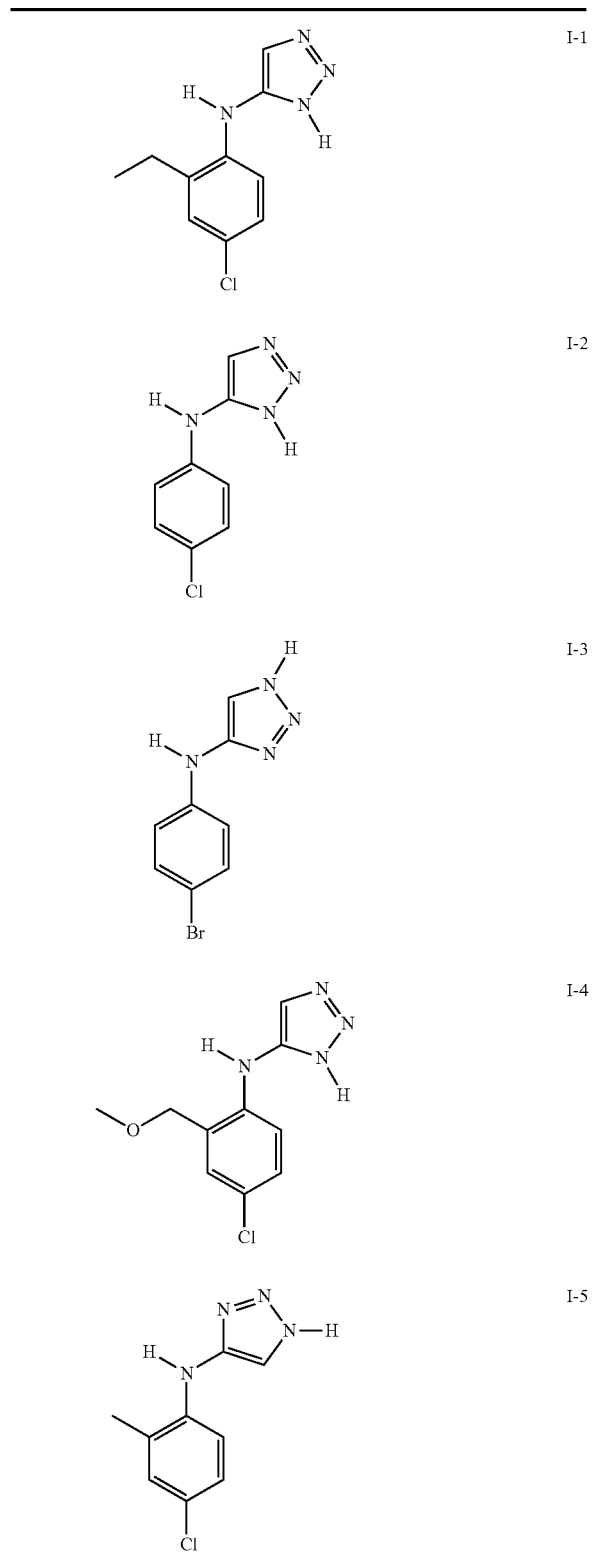
TABLE 1-continued TABLE 1-continued
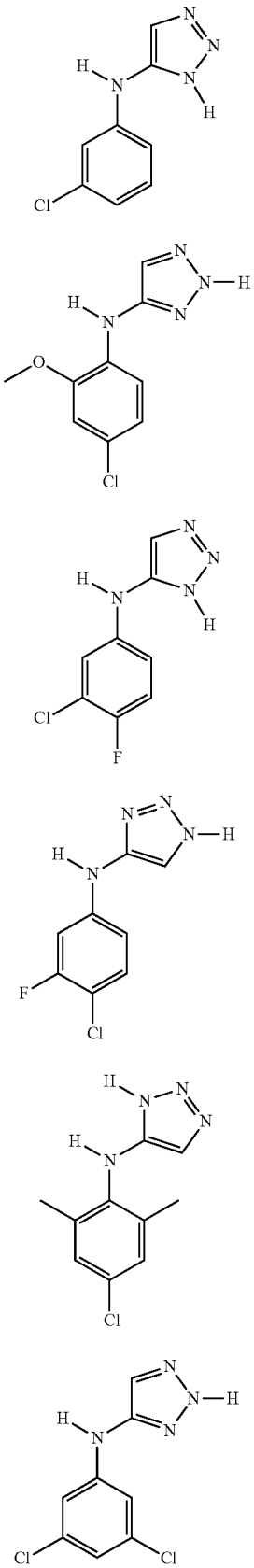
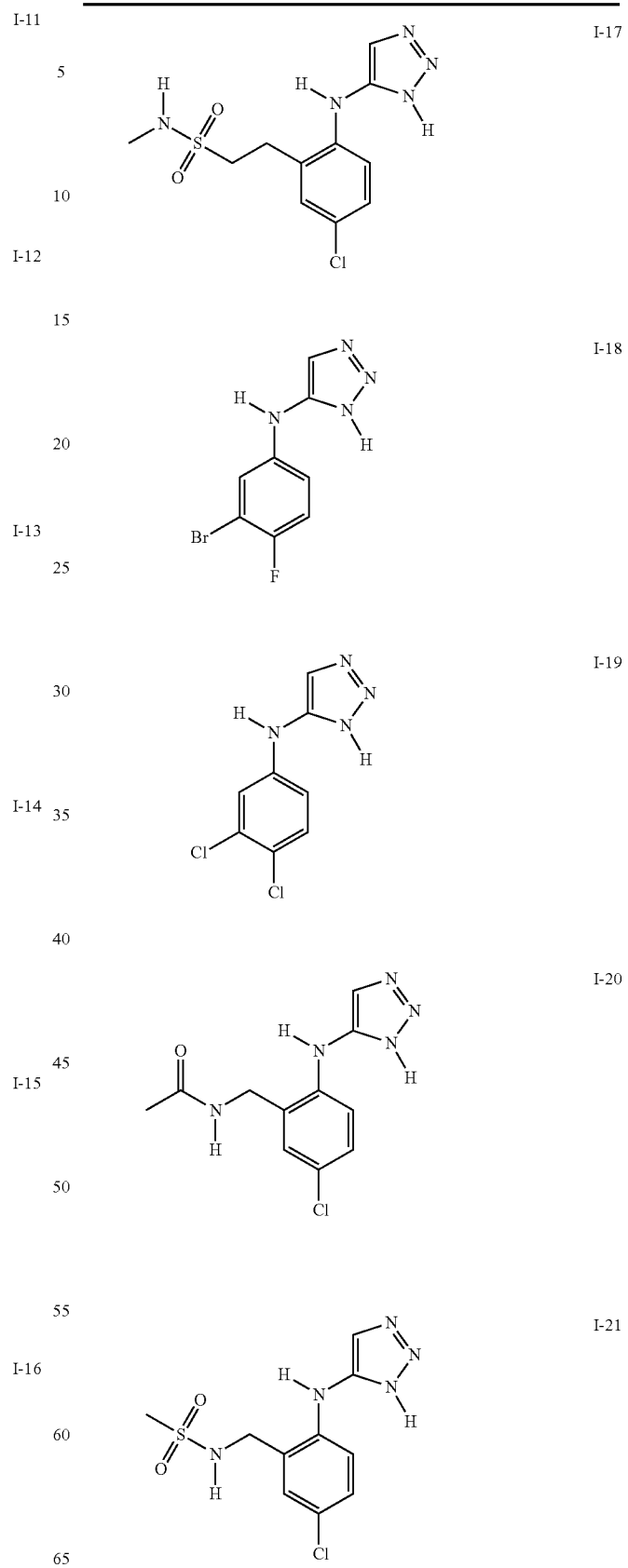

TABLE 1-continued
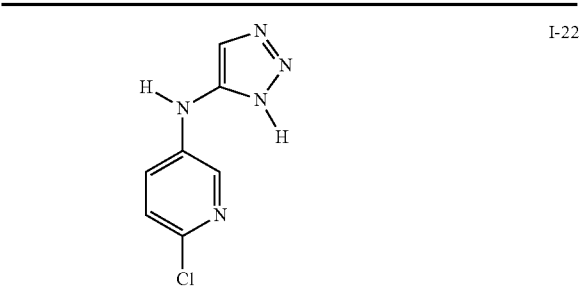 I-22
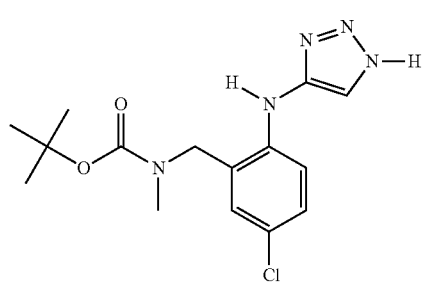 [SMILES: CN(Cc1cc(Cl)ccc1Nc1c[nH]nn1)C(=O)OC(C)(C)C] I-23
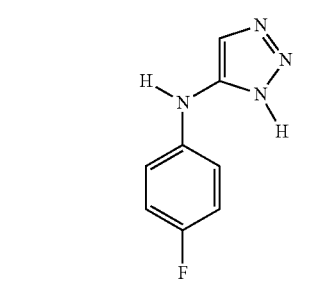 [SMILES: Fc1ccc(Nc2cnn[nH]2)cc1] I-24
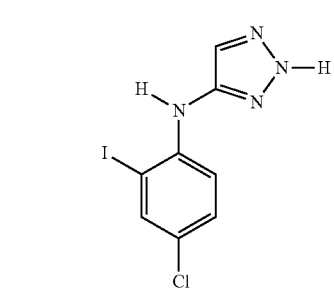 [SMILES: Clc1ccc(Nc2cn[nH]n2)c(I)c1] I-25
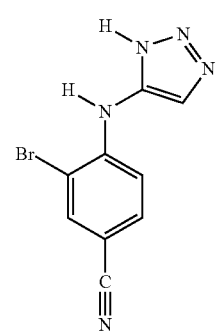 [SMILES: N#Cc1ccc(Nc2cnn[nH]2)c(Br)c1] I-26
TABLE 1-continued
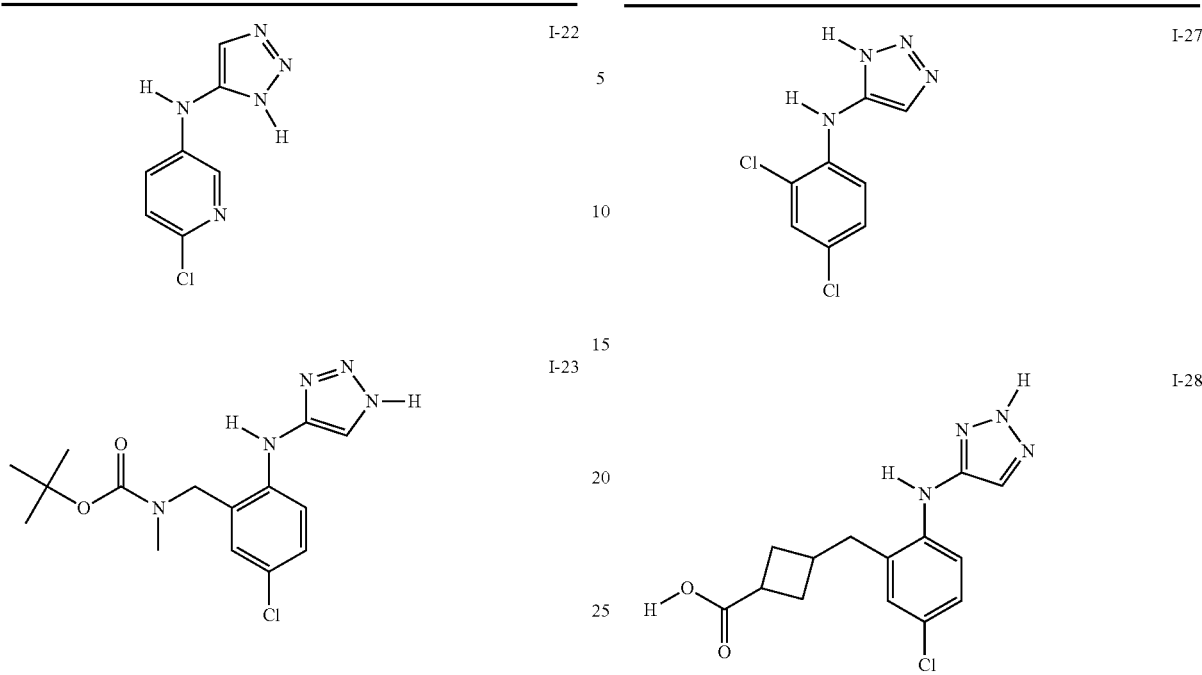 I-27
I-28
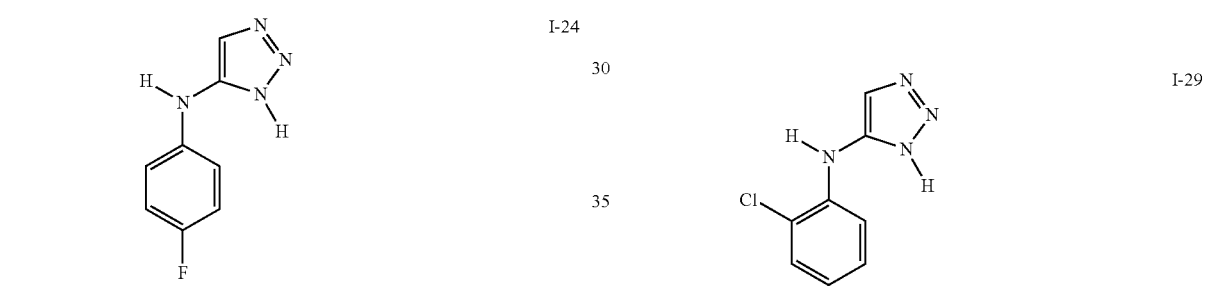 I-29
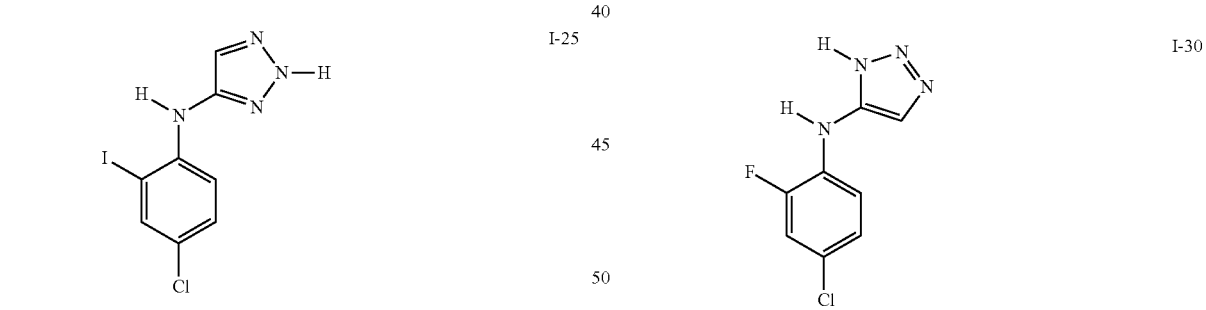 I-30
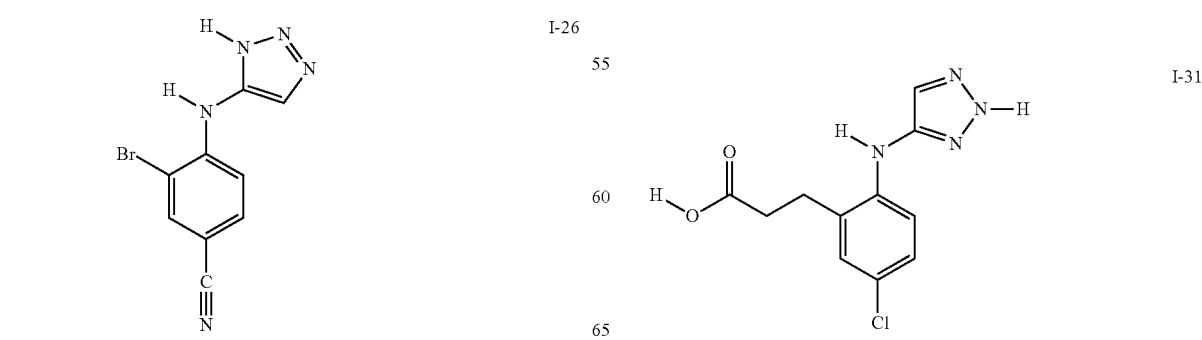 I-31

TABLE 1-continued
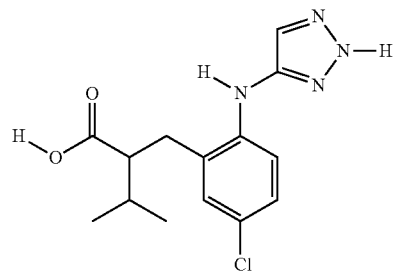 [SMILES: CC(C)C(Cc1cc(Cl)ccc1Nc1cn[nH]n1)C(=O)O] I-32
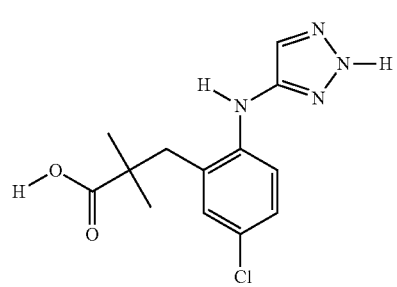 [SMILES: CC(C)(Cc1cc(Cl)ccc1Nc1cn[nH]n1)C(=O)O] I-33
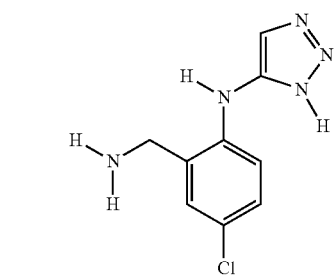 [SMILES: NCc1cc(Cl)ccc1Nc1cnn[nH]1] I-34
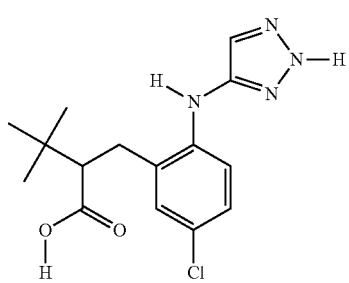 [SMILES: CC(C)(C)C(Cc1cc(Cl)ccc1Nc1cn[nH]n1)C(=O)O] I-35
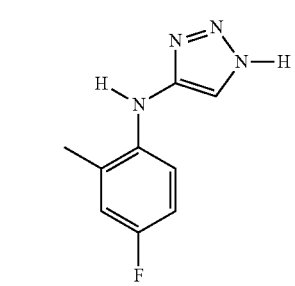 I-36
TABLE 1-continued
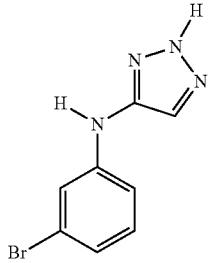 I-37
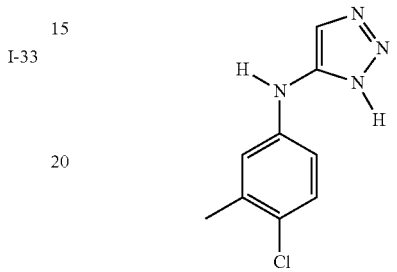 I-38
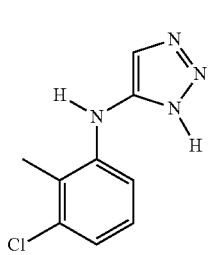 I-39
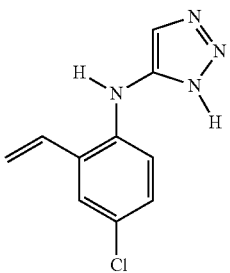 I-40
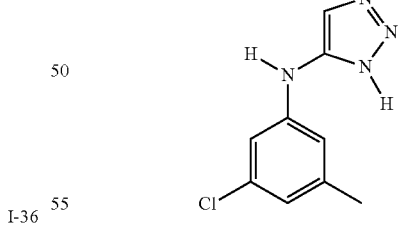 I-41
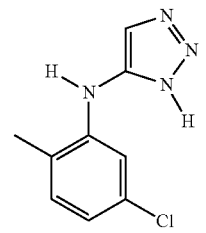 I-42

TABLE 1-continued

| | |
|---|---|
| 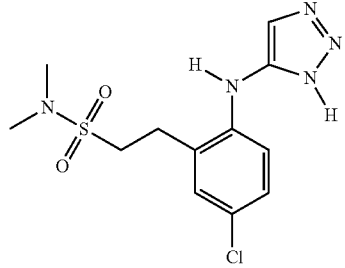 | I-43 |
| 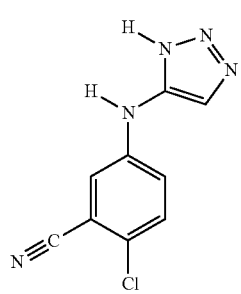 [SMILES: N#Cc1cc(Nc2cnn[nH]2)ccc1Cl] | I-44 |
| 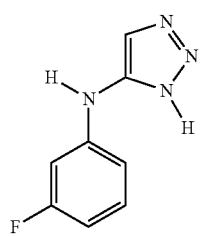 [SMILES: Fc1cccc(Nc2cnn[nH]2)c1] | I-45 |
| 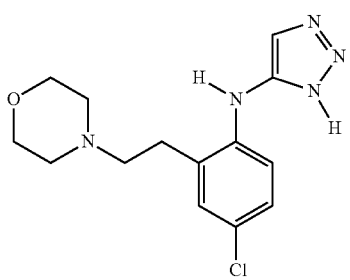 [SMILES: Clc1ccc(Nc2cnn[nH]2)c(CCN2CCOCC2)c1] | I-46 |
| 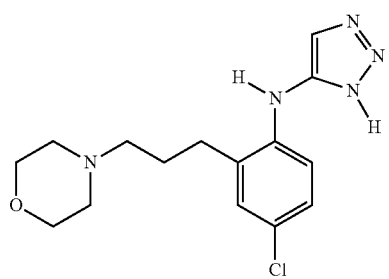 [SMILES: Clc1ccc(Nc2cnn[nH]2)c(CCCN2CCOCC2)c1] | I-47 |

TABLE 1-continued

| | |
|---|---|
| 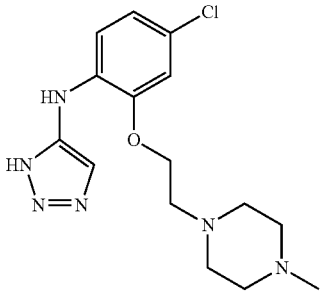 [SMILES: CN1CCN(CCOc2cc(Cl)ccc2Nc2cnn[nH]2)CC1] | I-48 |

Compounds of this invention include those described generally herein and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed.: Smith and March, John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as those illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl") refers to a monocyclic C3-C8 hydrocarbon or bicyclic C8-C12 hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially saturated or fully unsaturated. Examples of partially unsaturated groups include, but are not limited to, butene, cyclohexene, and tetrahydropyridine. Examples of fully unsaturated groups include, but are not limited to, phenyl, cyclooctatetraene, pyridyl, and thienyl.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene and Wuts, "Protective Groups in Organic Synthesis", Third Edition, John Wiley & Sons, New York: 1999, the entire contents of which are hereby incorporated by reference.

The term "cross-coupling", as used herein, refers to a reaction in which a carbon-nitrogen bond is formed with the aid of a metal catalyst or base. Examples of reactions that form carbon-nitrogen bonds, e.g., Chan-Lam couplings, Buchwald couplings and Buchwald Hartwig couplings, are described herein.

Buchwald or Buchwald-Hartwig coupling conditions involve the use of a palladium catalyst, a base, and a suitable solvent. Examples of suitable catalysts include, but are not limited to, (Pd[P(o-Tolyl)$_3$]$_2$), Pd$_2$(dba)$_3$, Pd(dba)$_2$, and [2-(2-aminoethyl)phenyl]-chloro-palladium; tBuXPhos. Suitable solvents include, but are not limited to, toluene, dioxane, and THF. Optional bases include NaOtBu or LiHMDS. Sometimes a bidentate phosphine ligand, e.g., BINAP or DPPF, can also be included.

Chan-Lam coupling conditions involve the use of copper acetate, a base, and a suitable solvent. Suitable bases include, but are not limited to, triethylamine and pyridine. Suitable solvents include, but are not limited to, dichloromethane and toluene.

Chan-Lam, Buchwald, and Buchwald-Hartwig coupling conditions are known to one skilled in the art and are described in more detail in a variety of references.

Unless otherwise indicated, a substituent connected by a bond drawn from the center of a ring means that the substituent can be bonded to any position in the ring. In example i below, for instance, J$^1$ can be bonded to any position on the pyridyl ring. For bicyclic rings, a bond drawn through both rings indicates that the substituent can be bonded from any position of the bicyclic ring. In example ii below, for instance, J$^1$ can be bonded to the 5-membered ring (on the nitrogen atom, for instance), and to the 6-membered ring.

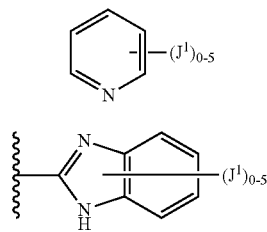

i ii

In some embodiments, a methylene unit of an alkyl or aliphatic chain is optionally replaced with another atom or group. Examples of such atoms or groups include, but are not limited to, —NR—, —O—, —C(O)—, —C(=N—CN)—, —C(=NR)—, —C(=NOR)—, —S—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRC(O)—, —NRC(O)O—, —SO$_2$NR—, —NRSO$_2$—, —NRC(O)NR—, —OC(O)NR—, and —NRSO$_2$NR—, wherein R is defined herein.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain.

For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to an H on the terminal end. For example, if a methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH. In another example, if a methylene unit of —CH$_2$CH$_2$CH$_3$ was optionally replaced with —NH—, the resulting compound could be —NHCH$_2$CH$_3$, —CH$_2$NHCH$_3$, or —CH$_2$CH$_2$NH$_2$.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

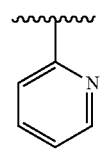 [SMILES: *c1ccccn1]

also represents

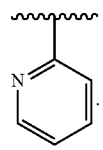

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Pharmaceutically Acceptable Salts, Solvates, Chlatrates, Prodrugs and other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts, e.g., compound I-34 described herein, might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

Abbreviations

The following abbreviations are used:
DMSO dimethyl sulfoxide
NMR nuclear magnetic resonance
HPLC high performance liquid chromatography
LCMS liquid chromatography-mass spectrometry
Rt retention time
DCM dichloromethane
THF tetrahydrofuran
LiHMDS lithium bis(trimethyl)amide
PS-DEAM polymer bound diethanolamine
DMEM Dulbecco's Modified Eagle Media Compound Uses One aspect of this invention provides compounds or compositions that are inhibitors of indoleamine 2,3-dioxygenase (IDO), or pharmaceutically acceptable salts thereof, and thus are useful for treating or lessening the severity of a disease, condition, or disorder in a patient, wherein IDO is implicated in the disease, condition, or disorder.

The terms, "disease", "disorder", and "condition" may be used interchangeably here to refer to an IDO mediated medical or pathological condition.

The term "IDO mediated condition", as used herein, means any disease state or other deleterious condition in which IDO is known to play a role. The term "IDO mediated condition" or "disease" also means those diseases or conditions that are alleviated by treatment with an IDO inhibitor. Such conditions include cancer and sepsis.

As used herein, the terms "subject" and "patient" are used interchangeably. The terms "subject" and "patient" refer to an animal, and more specifically a human. In one embodiment, the subject is a non-human animal such as a rat or dog. In a preferred embodiment, the subject is a human.

Another aspect of this invention provides compounds that are useful for the treatment of diseases, disorders, and conditions, e.g., viral disease, pneumonia, bacteremia, trauma, tuberculosis, parasitic disease, neuroinflammation, schizophrenia, depression, neurodegenerative disease, and pain.

Examples of neurodegenerative diseases include, without limitation, Alzheimer's disease, Parkinson's disease, Amyotrophic Lateral Sclerosis (ALS), Dementia, Multiple Sclerosis, and Huntington's disease.

Examples of viral diseases include, without limitation, Human Immunodeficiency Virus (HIV), Hepatitis A-D, Human Papilloma Virus (HPV), and Herpes, including Herpes Simplex I and II, as well as the Epstein Barr Virus.

Another aspect of this invention provides compounds that are useful for the treatment of diseases, disorders, and conditions, e.g., sepsis.

Another aspect of this invention provides compounds that are useful for the treatment of diseases, disorders, and conditions characterized by excessive or abnormal cell proliferation. Such diseases include a proliferative or hyperproliferative disease. Examples of proliferative and hyperproliferative diseases include, without limitation, cancer and myeloproliferative disorders.

In some embodiments, said compounds are selected from the group consisting of a compound of formula I. The term "cancer" includes, but is not limited to the following cancers. Oral: head and neck, including buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: Non-small cell lung carcinoma including adenocarcinoma (acinar, bronchioloalveolar carcinoma [nonmucinous, mucinous, mixed], papillary, solid adenocarcionoma, clear cell, mucinous [colloid] adenocarcinoma, mucinous cystadenocarcinoma, signet ring, well-differentiated fetal), bronchioalveolar, squamous cell carcinoma (basaloid, clear cell, papillary, small cell), large cell (undifferentiated) carcinoma (giant cell, basaloid, clear cell, large cell [with rhabdoid phenotype], large cell neuroendocrine carcinoma [LCNEC], combined LCNEC); small cell lung cancer including small cell (oat cell) carcinoma, combined small cell; adenoid cystic carcinoma; hamartoma; lymphoma; neuroendocrine/ carcinoid; sarcoma. Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Female/ Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast;

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

Thus, the term "cancerous cell" as provided herein, includes a cell afflicted by any one of the above-identified conditions. In some embodiments, the cancer is selected from head and neck, ovarian, melanoma cervical, endometrial, esophageal, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound of this invention, or a pharmaceutically acceptable salt thereof, and the additional therapeutic agent. Alternatively, those additional agents may be administered separately, as part of a multiple dosage regimen, from the IDO inhibitor-containing compound or composition. Furthermore, those agents may be part of a single dosage form or mixed together with the IDO inhibitor in a single composition.

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a subject.

In some embodiments, said additional therapeutic agent is selected from an anti-cancer agent, an anti-proliferative agent, or a chemotherapeutic agent.

In some embodiments, said additional therapeutic agent is selected from cisplatin (Platinol®), carboplatin (Paraplatin®), oxaliplatin (Eloxatin®), daunomycin (Daunorubicin®, DanuoXome®, Cerubidine®), doxorubicin (Adriamycin®, Rubex®), epirubicin (Ellence®), idarubicin (Idamycin®), valrubicin (Valstar®), mitoxantrone (Novantrone®), paclitaxel (Taxol®), docetaxel (Taxotere®) and cyclophosphamide (Cytoxan®).

In other embodiments, said additional therapeutic agent is selected from anti-cancer antibody or immunoglobulin therapies or agents including, but not limited to, ipilimumab (Yervoy®, Bristol-Myers Squibb), tremelimumab (Pfizer), antibodies or agents that target programmed death receptor 1 [PD-1] or programmed death ligand 1 [PD-L1], e.g., CT-011 (Curetech), BMS-936558 (Bristol-Myers Squibb), BMS-936559 (Bristol-Myers Squibb), AMP-224 (Amplimmune/Glaxo-Smithkline), or MGA-271 (Macrogenics).

In other embodiments, said additional therapeutic agent is an immune enhancer such as a vaccine, immune-stimulating antibody, immunoglobulin, agent or adjuvant including, but not limited to, sipuleucel-t (Provenge®, Dendreon Corporation), BMS-663513 (Bristol-Myers Squibb), CP-870893 (Pfizer/VLST), anti-OX40 (AgonOX), or CDX-1127 (CellDex).

Other cancer therapies or anticancer agents that may be used in combination with the inventive agents of the present invention include surgery, radiotherapy (e.g., gamma-radiation, neutron beam radiotherapy, electron beam radiotherapy, proton therapy, brachytherapy, low-dose radiotherapy, and systemic radioactive isotopes), immune response modifiers such as chemokine receptor antagonists, chemokines and cytokines (e.g., interferons, interleukins, tumour necrosis factor (TNF), and GM-CSF)), hyperthermia and cryotherapy, agents to attenuate any adverse effects (e.g. antimetics, steroids, anti-inflammatory agents), and other approved chemotherapeutic drugs.

A compound of the instant invention may also be useful for treating cancer in combination with or in addition to any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®);

leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglist-frame.htm, and The Merck Manual, Seventeenth Ed. 1999, the entire contents of which are hereby incorporated by reference.

Another aspect of this invention is directed towards a method of treating sepsis in a subject in need thereof, comprising the sequential or co-administration of a compound of this invention, or a pharmaceutically acceptable salt thereof, and one or more additional therapeutic agents. In other embodiments, those additional agents may be administered separately, as part of a multiple dosage regimen, from the IDO inhibitor-containing compound or composition. Alternatively, those agents may be part of a single dosage form or mixed together with the IDO inhibitor in a single composition.

In another aspect of the invention, said one or more additional therapeutic agents is selected from an antibiotic, a vasopressor, a steroid, an inotrope, an anti-thrombotic agent, a sedative, opioids, or an anesthetic.

In other embodiments, said one or more additional therapeutic agents is selected from cephalosporins, macrolides, penams, beta-lactamase inhibitors, aminoglycoside antibiotics, fluoroquinolone antibiotics, glycopeptide antibiotics, penems, monobactams, carbapenmems, nitroimidazole antibiotics, lincosamide antibiotics, vasopressors, positive inotropic agents, steroids, benzodiazepines, phenol, alpha2-adrenergic receptor agonists, GABA-A receptor modulators, anti-thrombotic agents, anesthetics, or opioids.

A compound of the instant invention may also be useful for treating sepsis along with any of the following therapeutic agents: Alatrofloxacin, Amifloxacin, Balofloxacin, Besifloxacin, Ciprofloxacin, Clinafloxacin, Danofloxacin, Delafloxacin, Difloxacin, Enoxacin, Enrofloxacin, Fleroxacin, Garenoxacin, Gatifloxacin, Gemifloxacin, Grepafloxacin, Levofloxacin, Lomefloxacin, Marbofloxacin, Moxifloxacin, Nadifloxacin, Norfloxacin, Ofloxacin, Orbifloxacin, Pazufloxacin, Pefloxacin, Prulifloxacin, Rufloxacin, Sitafloxacin, Sparfloxacin, Temafloxacin, Tosufloxacin, Trovafloxacin, Vancomycin, Teicoplanin, Telavancin, Bleomycin, Ramoplanin, Decaplanin, Azanidazole, Dimetridazole, Metronidazole, Nimorazole, Ornidazole, Propenidazole, Secnidazole, Tinidazole, Linomycin, Clindamycin, Cefazolin, Cefacetril(e), Cefadroxil, Cefalexin, Cefaloglycin, Cefalonium, Cefaloridin(e), Cefaoltin, Cefapirin, Cefatrizin(e), Cefazedon(e), Cefazaflur, Cefradin(e), Cefroxadin(e), Ceftezol(e), Cefaclor, Cefamandole, Cefminox, Cefonicid, Ceforanide, Cefotiam, Cefprozil, Cefbuperazone, Cefuroxime, Cefuzonam, Cephamycin (Cefoxitin, Cefotetan, Cefmetazole), Carbacephem (Loracarbef), Cefixime, Ceftriaxome, Ceftazidime, Cefoperazone, Cefcapene, Cefdaloxime, Cefdinir, Cefditoren, Cafatamet, Cefmenoxime, Cefodizime, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftobiprole, Ceftaroline fosamil, Amoxicillin, Ampicillin, Epicillin, Carbenicillin, e.g., Carindacillin, Ticarcillin, Temocillin, Azlocillin, Piperacillin, Mezlocillin, Mecillinam, Sulbenicillin, Benylpenicillin, Clometocillin, Benzathine benylpenecillin, Procaine benylpenecillin, Azidocillin, Penamecillin, Phenoxymethylpenecillin, Propicillin, Benzathine phenoxymthylpenecillin, Pheneticillin, Cloxacillin, Oxacillin, Meticillin, Nafcillin, Faropenem, Aztreonam, Tigemonam, Carumonam, Nocardicin A, Biapenem, Ertapenem, Antipseudomonal, Panipenem, Penam, Clavam, Azithromycin, Clarithromycin, Dirithromycin, Erythromycin, Kitasamycin, Midecamycin, Roxithromycin, Troleandomycin, Ansamycin, Carbomycin, Cethromycin, Oleandomycin, Solithromycin, Spiramycin, Telithromycin, Tylosin, Amikacin, Arbekacin, Gentamicin, Kanamycin, Neomycin, Netilmicin, Paromycin, Rhodostreptomycin, Streptomycin, Tobramycin, Apramycin, Norepinephrine, Epinephrine, Phenylepinephrine, Dopamine, Vasopressin, Berberine, Calcium, Omecamtiv, Dobutamine, Dopexamine, Isoprenaline, Phenylepinephrine, Dogoxin, Prostaglandins, Enoximone, Milrinone, Amrinone, Theophylline, Digitalis, Glucagon, Hydrocortisone, Cortisone, Fluorocortisone, Heparin, Diazepam, Lorazepam, Midazolam, Propofol, Dexmedetomidine, Etomidate, Fentanyl, Hydromorphone, Morphine, Meperidine, Remifentanil, or Ketamine.

Other examples of agents the compounds of this invention may also be combined with, or used in addition to, include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating blood disorders such as corticosteroids, anti-leukemic agents, and growth factors; and agents for treating immunodeficiency disorders such as gamma globulin.

Depending upon the particular IDO-mediated conditions to be treated or prevented, additional drugs, which are normally administered to treat or prevent that condition, may be administered together with the compounds of this invention.

Compositions for Administration into a Subject

The IDO inhibitors or pharmaceutical salts thereof may be formulated into pharmaceutical compositions for administration to animals or humans. These pharmaceutical compositions, which comprise an amount of the IDO inhibitor effective to treat or prevent an IDO mediated condition and a pharmaceutically acceptable carrier thereof, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of IDO inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Biological Samples

As inhibitors of IDO activity, the compounds and compositions of this invention are also useful in biological samples. One aspect of the invention relates to inhibiting IDO activity in a biological sample, which method comprises contacting said biological sample with a compound of formula I-A or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of IDO activity in a biological sample is useful for a variety of purposes that are known to one of skill in the art. Examples of such purposes include, but are not limited to, cancer treatment.

Study of IDO

Another aspect of this invention relates to the study of IDO in biological and pathological phenomena; the study of intracellular signal transduction pathways mediated by IDO; and the comparative evaluation of new IDO inhibitors. Examples of such uses include, but are not limited to, biological assays such as enzyme assays and cell-based assays.

The activity of the compounds as IDO inhibitors may be assayed in vitro or in vivo. In vitro assays include assays that quantitate the ability of the inhibitor to bind to IDO and may be determined by measuring the production of kynurenine. Detailed conditions for assaying a compound utilized in this invention as an inhibitor of IDO is set forth in the Examples below.

Another aspect of the invention provides a method for modulating enzyme activity by contacting a compound of formula I-A with IDO.

Methods of Treatment

In one aspect, the present invention provides a method for treating or lessening the severity of a disease, condition, or disorder where IDO is implicated in the disease state. In another aspect, the present invention provides a method for treating or lessening the severity of an IDO mediated disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to IDO. Another aspect provides a method for treating or lessening the severity of an IDO mediated disease, condition, or disorder by inhibiting enzymatic activity of IDO with an IDO inhibitor.

In another aspect, the present invention provides a method for inhibiting IDO activity in a patient comprising administering to the patient a compound or composition of the present invention. In another embodiment, the present invention provides a method for inhibiting IDO activity in a biological sample comprising administering a compound or composition of the present invention.

One aspect of the invention relates to a method of inhibiting IDO activity in a patient, which method comprises administering to the patient a compound described herein, or a composition comprising said compound. In some embodiments, the method is used to treat or prevent a condition selected from a proliferative or hyperproliferative disease, e.g., cancer. In another embodiment, the method is used to treat or prevent sepsis.

Another aspect of the invention provides a method of treating, preventing, or lessening the severity of a disease or condition of a patient selected from cancer, proliferative disorder, viral disease, sepsis, pneumonia, bacteremia, trauma, tuberculosis, parasitic disease, neuroinflammation, schizophrenia, depression, neurodegenerative disease, and pain, by administering a compound or composition of the present invention. In another embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an anti-viral agent, an agent for treating blood disorders, or an agent for treating immunodeficiency disorders, wherein said additional therapeutic agent is appropriate for the disease being treated; and said additional therapeutic agent is administered together with the composition as a single dosage form or separately from said composition as part of a multiple dosage form.

Experimental Materials and Methods

All commercially available solvents and reagents were used as received. $^1$H-NMR spectra were recorded at 500 MHz using a Bruker Ascend 500 instrument. Mass spec.

samples were analyzed on a MicroMass Quattro Micro mass spectrometer operated in single MS mode with electrospray ionization. Where stated, purification of final compounds were executed using FractionLynx™ HPLC mass directed purification or ISCO CombiFlash® Companion.

As used herein, the term "Rt(min)" refers to the HPLC retention time, in minutes, associated with the compound. Unless otherwise indicated, the HPLC methods utilized to obtain the reported retention times are as described below:

HPLC Method

Instrument: Waters Acquity UPLC-MS

Column: Waters UPLC BEH C8 1.7 µm, 2.1×50 mm with Vanguard BEH C8 1.7 µm, 2.1×5 mm guard column Column temperature: 45 C Mobile Phase A: 10 mM ammonium formate in water: acetonitrile 95:5, pH 9

Mobile Phase B: acetonitrile

Gradient: initial: 2% B, 0-1.15 min: 2% B to 98% B, 1.15-1.35 min: hold at 98% B, 1.35-1.40 min: 98% B to 2% B, 1.40-1.50 min: hold at 2% B Flow rate: 1.0 mL/minute Detection: 210-400 nm Mass spectrometer: Waters SQD with electrospray ionization operating in positive and negative ion mode.

SCHEMES AND EXAMPLES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance), described above. The generic schemes and examples, described below, illustrate how to prepare the compounds of the present disclosure. The examples are for the purpose of illustration only and are not to be construed as limiting the scope of the invention in any way.

Scheme 1: Approach 1 for the preparation of compounds I-A

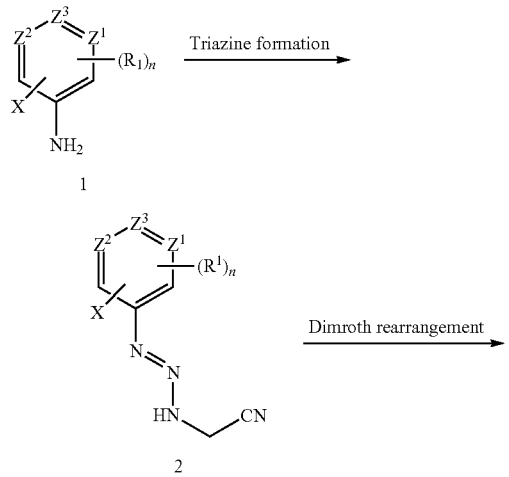

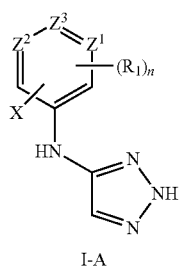

Scheme 1 shows one general route to compounds I-A. An appropriate aromatic amine 1 was diazotised with sodium nitrite to generate an intermediate diazonium species, which was further reacted with amino acetonitrile to generate a triazine 2. A one pot thermal ring closure followed by a Dimroth rearrangement provided the aminotriazole I-A.

Example 1

Preparation of of 5-((2H-1,2,3-triazol-4-yl)amino)-2-chlorobenzonitrile (compound I-44)

Step 1: 2-Chloro-5-(3-(cyanomethyl)triaz-1-en-1-yl)benzonitrile

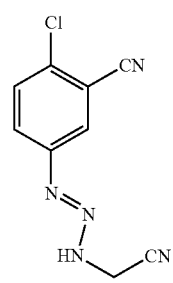

5-amino-2-chloro-benzonitrile (800 mg, 5.243 mmol) was dissolved in hydrochloric acid (12.06 mL of 2 M, 24.12 mmol) and diluted with water (16 mL) and cooled to 0° C. Sodium nitrite (362 mg, 167 µL, 5.24 mmol) was added and the reaction was stirred at 0° C. for 20 min and then a solution of 2-aminoacetonitrile monohydrochloride (485 mg, 5.24 mmol) in water (6 mL) was slowly added. The mixture was stirred for 10 min at 0° C. and sodium acetate (6.04 g, 73.61 mmol) was then added and the mixture allowed to warm to room temperature and stirred for 1 h. The precipitate was collected by filtration and washed with water to afford the title compound 2a as a tan colored solid. MS m/z: 220.1 (M+H)$^+$.

Step 2: 5-((2H-1,2,3-Triazol-4-yl)amino)-2-chlorobenzonitrile

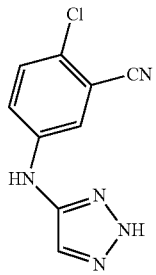

2-Chloro-5-(3-(cyanomethyl)triaz-1-en-1-yl)benzonitrile 2a (1.15 g, 5.24 mmol) was dissolved in EtOH (23 mL) and heated to reflux for 4 h. The mixture was allowed to cool to room temperature and then concentrated. The material was triturated with DCM to produce a cream solid which was purified by ISCO (30-40% EtOAc in hexanes) to afford the title compound I-44 as a yellow solid (231 mg, 20%). $^1$H NMR (500 MHz, d6-DMSO) δ 14.45 (1H, s), 9.33 (1H, s), 7.80 (1H, s), 7.65-7.39 (3H, m). MS m/z: 220.1 (M+H)$^+$.

The following aminotriazoles were synthesised using a similar procedure as outlined for Compound I-44: Compounds I-1, I-2, I-5, I-16, I-18, I-19, I-25, I-26, and I-37.

Scheme 2: Approach 2 for the preparation of compounds I-A

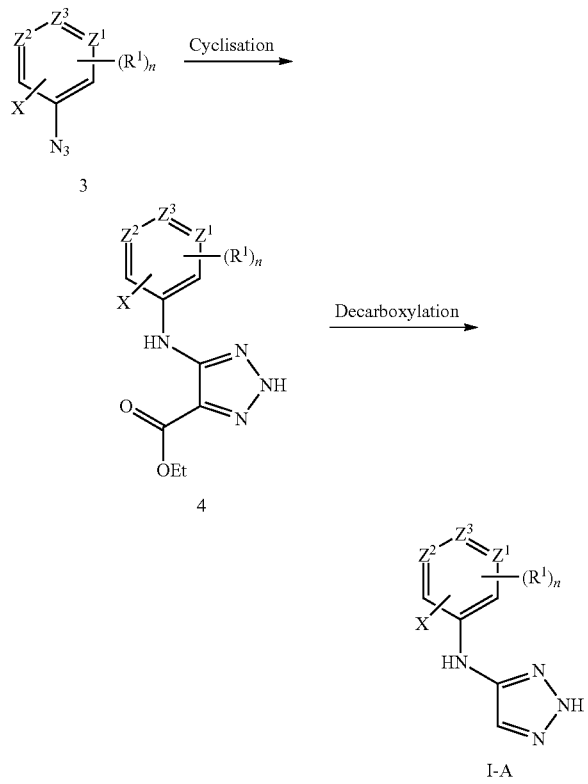

Scheme 2 shows an alternative route to compounds I-A. An appropriate aromatic azide 3 was cyclised with ethyl 2-cyanoacetate to provide the substituted 1,2,3-triazole 4. Basic ester hydrolysis and decarboxylation sequence provided the aminotriazole I-A.

Example 2

Preparation of of N-(3-chloro-4-fluorophenyl)-2H-1,2,3-triazol-4-amine (compound I-13)

Step 1: Ethyl 5-amino-1-(3-chloro-4-fluorophenyl)-1H-1,2,3-triazole-4-carboxylate

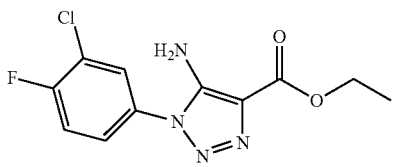

To a solution of ethyl 2-cyanoacetate (857.2 mg, 0.81 mL, 7.58 mmol) in EtOH (13 mL) was added sodium ethoxide (4.00 mL of 2 M in EtOH, 8.00 mmol). 4-azido-2-chloro-1-fluoro-benzene (1.0 g, 5.83 mmol) was added dropwise followed by additional EtOH (5 mL). The reaction was stirred for 1 h and then concentrated to afford the title compound 4a as a yellow solid (1.5 g, 88%). MS m/z: 254.8 (M−H)$^+$.

Step 2: N-(3-Chloro-4-fluorophenyl)-2H-1,2,3-triazol-4-amine

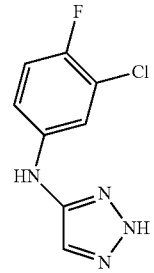 [SMILES: Fc1ccc(Nc2cn[nH]n2)cc1Cl]

Ethyl 5-amino-1-(3-chloro-4-fluorophenyl)-1H-1,2,3-triazole-4-carboxylate 4a (120.0 mg, 0.4 mmol) was suspended in aqueous NaOH (4.00 mL of 2 M, 8.00 mmol) and the solution heated to reflux and stirred for 3 h. The solution was allowed to cool and acidified with 1M HCl and then extracted into EtOAc and the organic layer concentrated. The residue was dissolved in DMSO (2 mL) and heated to 110° C. for 3 h. The mixture was allowed to cool and purified by FractionLynx to afford the title compound I-13 as a white solid (56.8 mg, 64%). $^1$H NMR (500 MHz, d6-DMSO) δ 8.74 (1H, brs), 7.48-7.50 (1H, m), 7.31 (1H, s), 7.20-7.24 (1H, m), 7.10-7.13 (1H, m). MS m/z: 212.9 (M+H)$^+$.

The following aminotriazoles were synthesised using a similar procedure as outlined for Compound I-13: Compounds I-3, I-11, I-14, I-24, I-29, and I-30.

39

Scheme 3: Approach 3 for the preparation of compounds I-A

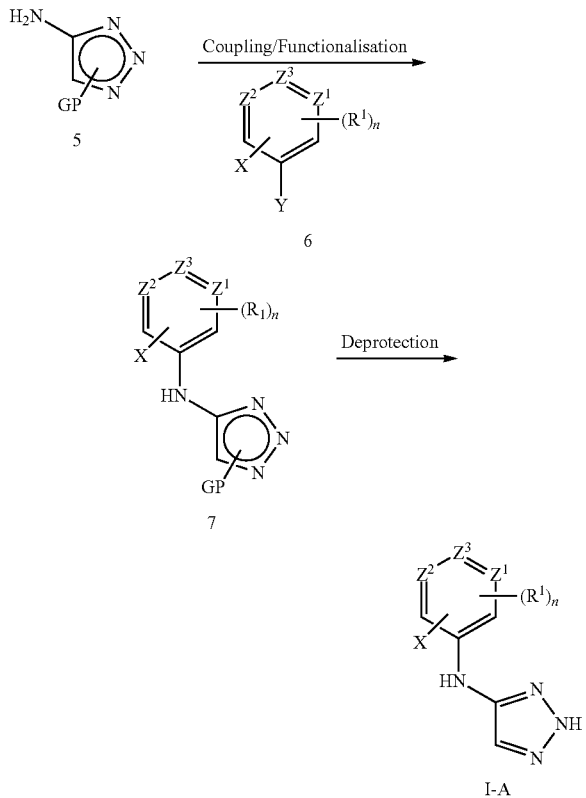

Scheme 3 shows an alternative route to compounds I-A. A suitably protected aminotriazole 5 was reacted with a suitably activated aromatic partner 6 (Y=Br, Cl, BOR$_2$; R is defined herein) to produce the coupled protected aminotriazole 7. Subsequent functional group manipulations, as required, and a triazole deprotection step provided the aminotriazole I-A.

Example 3

Preparation of Intermediate compound 5

Method 1: 1-Benzyl-1H-1,2,3-triazol-5-amine

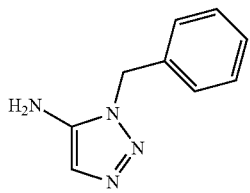

5a

A suspension of 5-amino-1-benzyl-triazole-4-carboxylic acid (5.00 g, 22.91 mmol) in N,N-dimethylaniline (23 mL) was heated to reflux and stirred for 20 min and then allowed to cool and stirred overnight at room temperature. The reaction was cooled in an ice bath and the solid precipitate was filtered, washed with hexanes, and air dried to afford the title compound 5a as an off white solid (1.90 g, 48%). $^1$H NMR (500 MHz, d6-DMSO) δ 7.33-7.35 (1H, m), 7.27-7.30 (1H, m), 7.18-7.21 (2H, m), 6.81 (1H, s), 5.58 (2H, brs), 5.35 (2H, s). MS m/z: 175.0 (M+H)$^+$.

Method 2: 2-((2-(Trimethylsilyl)ethoxy)methyl)-2H-1,2,3-triazol-4-amine 5b and 1-((2-(trimethylsilyDethoxy)methyl)-1H-1,2,3-triazol-4-amine 5c Step 1: 5-Nitro-2-((2-(trimethylsilyl)ethoxy)methyl)-1H-1,2,3-triazole and 4-nitro-1-((2-(trimethylsilyl)ethoxy)methyl)-1H-1,2,3-triazole To a solution of 4-nitro-1H-triazole (5.00 g, 43.84 mmol) in THF (230 mL), cooled to 0° C., was added sodium hydride (2.28 g, 56.99 mmol) portionwise over 30 min. The mixture was stirred for a further 30 min and then 2-(chloromethoxy)ethyl-trimethyl-silane (7.67 g, 8.15 mL, 46.03 mmol) was added dropwise. The reaction was allowed to warm to room temperature and stirred for 2 h, then re-cooled to 0° C. and quenched with water. The mixture was extracted with EtOAc and the organics washed with brine, dried (MgSO$_4$) and concentrated. The residue was purified by column chromatography eluting with 5% EtOAc in hexanes to afford 4-nitro-2-((2-(trimethylsilyl)ethoxy)methyl)-2H-1,2,3-triazole (6.18 g, 56%) and 4-nitro-1-((2-(trimethylsilyl)ethoxy)methyl)-1H-1,2,3-triazole as an off white solid (3.52 g, 33%).

Step 2a: 2-((2-(Trimethylsilyl)ethoxy)methyl)-2H-1,2,3-triazol-4-amine

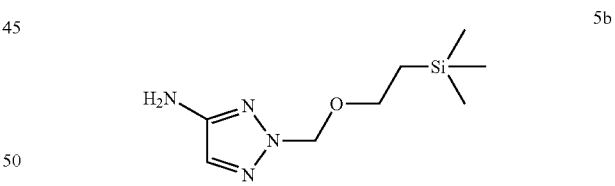

5b

To prepare a compound of 5b, a mixture of 4-nitro-2-((2-(trimethylsilyl)ethoxy)methyl)-2H-1,2,3-triazole (3.80 g, 15.55 mmol) and palladium on carbon [wet, Degussa] (1.66 g, 1.56 mmol) in MeOH (66 mL) was degased several times using vacuum/nitrogen cycles and then vacuum/hydrogen cycles and left under a hydrogen atmosphere for 18 h. The mixture was filtered through celite, the celite washed with methanol, and concentrated to afford 2-((2-(trimethylsilyl)ethoxy)methyl)-2H-1,2,3-triazol-4-amine 5b as a colorless oil (3.12 g, 94%). $^1$H NMR (500 MHz, d6-DMSO) δ 7.03 (1H, s), 5.40 (2H, s), 5.13 (2H, s), 3.58 (2H, dd), 0.85 (2H, dd), 0.01 (9H, s).

Step 2b: 1-((2-(Trimethylsilyl)ethoxy)methyl)-1H-1,2,3-triazol-4-amine

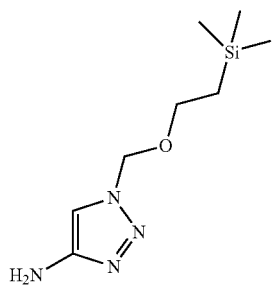

5c

To prepare a compound of 5c, a mixture of 4-nitro-1-((2-(trimethylsilyl)ethoxy)methyl)-1H-1,2,3-triazole (1.2 g, 4.91 mmol) and palladium on carbon [wet, Degussa] (523 mg, 0.49 mmol) in MeOH (21 mL) was degased several times using vacuum/nitrogen cycles and then vacuum/hydrogen cycles and left under a hydrogen atmosphere for 18 h. The mixture was filtered through celite, the celite washed with methanol, and concentrated to afford 1-((2-(trimethylsilyl)ethoxy)methyl)-1H-1,2,3-triazol-4-amine 5c as an off white solid (1.04 g, 98%). $^1$H NMR (500 MHz, d6-DMSO) δ 7.20 (1H, s), 5.51 (2H, s), 4.78 (2H, s), 3.53 (2H, dd), 0.86 (2H, dd), 0.00 (9H, s).

Example 4

Preparation of (2-((2H-1,2,3-triazol-4-yl)amino)-5-chlorophenyl)methanol (compound I-9)

Step 1: [2-[(3-Benzyltriazol-4-yl)amino]-5-chlorophenyl]methanol

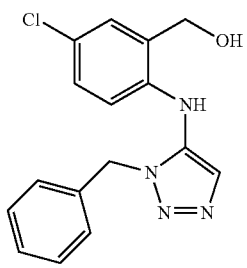

7a

Preparation of 2-((1-benzyl-1H-1,2,3-triazol-5-yl)amino)-5-chlorobenzoic acid: A solution of 1-benzyl-1H-1,2,3-triazol-5-amine 5a (1.00 g, 5.74 mmol) in THF (10 mL) was cooled to −78° C. LiHMDS (14.35 mL of 1M in THF, 14.35 mmol) was added dropwise. Upon complete addition 4-chloro-2-fluoro-benzoic acid (1.00 g, 5.74 mmol) in THF (5 mL) was added and the mixture stirred at −78° C. for 10 min and allowed to warm to room temperature and then heated at 100° C. for 20 h. The mixture was then treated with water (10 mL) and concentrated. The residue was partitioned between EtOAc and 1M HCl and the organic layer dried (Na$_2$SO$_4$) and concentrated to afford 2-((1-benzyl-1H-1,2,3-triazol-5-yl)amino)-5-chlorobenzoic acid (1.89 g, quant). MS m/z: 329.1 (M+H)$^+$.

Preparation of [2-[(3-benzyltriazol-4-yl)amino]-5-chlorophenyl]methanol: A solution of 2-((1-benzyl-1H-1,2,3-triazol-5-yl)amino)-5-chlorobenzoic acid (965 mg, 2.94 mmol) in THF (7.5 mL) was treated with borane (14.68 mL of 1M in THF, 14.68 mmol). The reaction was stirred for 21 h before adding additional borane (4.4 mL of 1M in THF, 4.40 mmol) and stirring for an additional 1 h. The reaction was quenched with water and concentrated. The residue was then stirred in 3M Methanolic HCl for 1 h and then concentrated. The residue was partitioned between EtOAc and water and the organic layer dried (MgSO$_4$) and concentrated to afford the title compound 7a (895 mg, 97%). MS m/z: 315.1 (M+H)$^+$.

Step 2: (2-((2H-1,2,3-Triazol-4-yl)amino)-5-chlorophenyl)methanol

A solution of [2-[(3-benzyltriazol-4-yl)amino]-5-chlorophenyl]methanol 7a (300 mg, 0.95 mmol) in MeOH (5 mL) was treated with formic acid (1.00 mL, 26.51 mmol). The mixture was degassed by vacuum/nitrogen cycles before the addition of palladium on carbon (507.1 mg, 0.48 mmol). The mixture was stirred under an argon atmosphere at room temperature for 18 h and then filtered through celite and concentrated. The material was purified by FractionLynx to afford the title compound I-9 as a solid (90.0 mg, 40%). 1H NMR (500 MHz, DMSO) δ 14.20 (1H, s), 7.85-7.80 (1H, s), 7.60 (1H, s), 7.51 (1H, s), 7.31 (1H, d), 7.19 (1H, d), 4.55 (2H, s). MS m/z: 223.1 (M−H)$^+$.

Example 5

Preparation of N-(2-(aminomethyl)-4-chlorophenyl)-2H-1,2,3-triazol-4-amine (compound I-34)

Step 1: N-[2-(Aminomethyl)-4-chloro-phenyl]-3-benzyl-triazol-4-amine

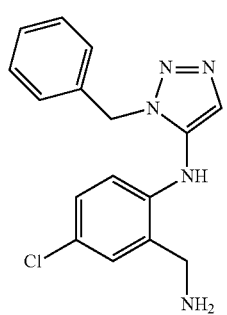

7b

Preparation of 2-[(3-benzyltriazol-4-yl)amino]-5-chloro-benzonitrile:—1-Benzyl-1H-1,2,3-triazol-5-amine 5a (1.00 g, 5.74 mmol) and 5-chloro-2-fluoro-benzonitrile (892.9 mg, 5.74 mmol) were combined in THF (6 mL) and cooled to −78° C. LiHMDS (6.31 mL of 1 M, 6.31 mmol) was added dropwise and the reaction stirred for 5 min and then allowed to warm to room temperature and subsequently heated at 60° C. for 1 h. The mixture was quenched water and then evaporated and the residue partitioned between EtOAc and 1M HCl, the organic layer separated and concentrated. Trituration of the residue in EtOAc and hexanes afforded 2-[(3-benzyltriazol-4-yl)amino]-5-chloro-benzonitrile as a brown solid (1.06 g, 60%). MS m/z: 310.1 (M+H)+.

Preparation of N-[2-(aminomethyl)-4-chloro-phenyl]-3-benzyl-triazol-4-amine:—A solution of 2-[(3-benzyltriazol-4-yl)amino]-5-chloro-benzonitrile (439 mg, 1.42 mmol) in THF (3 mL) was treated with borane (6.00 mL of 1 M in THF, 6.00 mmol) and then stirred at room temperature for 1 h. The mixture was then treated with water (5 mL) and concentrated before partitioning between EtOAc and water. The organic layer was concentrated and the resulting residue was stirred in 3M methanolic HCl for 1 h and then concentrated. The residue was partitioned between EtOAc and water and the organic layer separated and concentrated to afford the title compound 7b (439 mg, 99%). MS m/z: 314.2 (M+H)+.

Step 2: —N-(2-(Aminomethyl)-4-chlorophenyl)-2H-1,2,3-triazol-4-amine

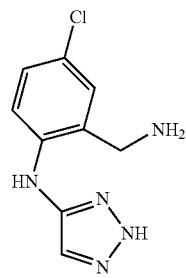 [SMILES: NCc1cc(Cl)ccc1Nc1cn[nH]n1]

A solution of N-[2-(aminomethyl)-4-chloro-phenyl]-3-benzyl-triazol-4-amine 7b (439 mg, 1.40 mmol) in dry MeOH (18 mL) and EtOAc (18 mL) was treated with dibromozinc (126.0 mg, 0.56 mmol). The degassed mixture was then treated with 10% palladium on carbon (297.8 mg, 0.28 mmol) before affixing a hydrogen balloon. The mixture was stirred at room temperature for 2 h before filtering through celite and concentrating. The material was purified on an ISCO (0-100% MeOH in DCM) and the freebase was stirred in 4N HCl in dioxane for 30 min before evaporating to afford the title compound I-34 (mono hydrochloride salt) as a solid (291 mg, 80%). 1H NMR (500 MHz, DMSO-d6) δ 8.52 (1H, s) 8.47 (3H, m), 7.63 (1H, d), 7.53 (s, 1H), 7.48 (1H, d), 7.31 (1H, d) 4.12 (2H, q). MS m/z: 224.1 (M+H)+.

Example 6

Preparation of N-(2-((2H-1,2,3-triazol-4-yl)amino)-5-chlorobenzyl)acetamide (compound I-20)

Step 1: N-[[2-[(3-Benzyltriazol-4-yl)amino]-5-chloro-phenyl]methyl]acetamide

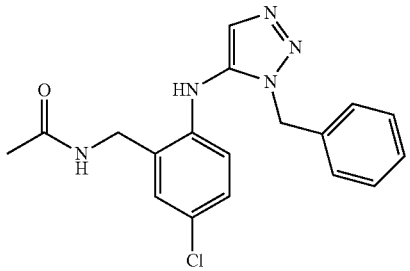

7c

A solution of N-[2-(aminomethyl)-4-chloro-phenyl]-3-benzyl-triazol-4-amine (as described in Example 5) (512 mg, 1.63 mmol) and triethylamine (495 mg, 682 µL, 4.90 mmol) in THF (15 mL) was treated with acetyl chloride (128.1 mg, 116 µL, 1.63 mmol) and the mixture stirred at room temperature for 75 min. The reaction was then quenched with water and concentrated. The residue was partitioned between EtOAc and saturated aqueous sodium hydrogen carbonate and the organic layer was separated and concentrated. Purification by column chromatography (0-100% EtOAc in hexanes) afforded the title compound 7c (105 mg, 18%). MS m/z: 356.2 (M+H)+.

Step 2: N-(2-((2H-1,2,3-Triazol-4-yl)amino)-5-chlorobenzyl)acetamide

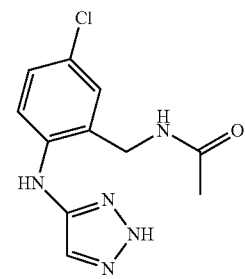 [SMILES: CC(=O)NCc1cc(Cl)ccc1Nc1cn[nH]n1]

N-[[2-[(3-Benzyltriazol-4-yl)amino]-5-chloro-phenyl]methyl]acetamide 7c (105 mg, 0.30 mmol) was dissolved in MeOH (5 mL) and treated with formic acid (367 mg, 301 µL, 7.97 mmol). The mixture was degassed by vacuum/nitrogen cycles before the addition of palladium on carbon (157 mg, 0.15 mmol). An argon balloon was affixed and the mixture was left to stir for 15 h before filtering through celite and concentrating. The material was purified by FractionLynx to afford the title compound I-20 (0.5 TFA salt) as a solid (28.2 mg, 29%). 1H NMR (500 MHz, DMSO) δ 8.53 (1H, t), 8.32-8.36 (1H, m), 7.61 (1H, d), 7.44 (1H, s), 7.15-7.25 (2H, m), 4.28 (2H, d), 1.93 (3H, s). MS m/z: 266.1 (M+H)+.

The following aminotriazoles were synthesised using a similar procedure as outlined for Compound I-20: Compound I-21.

Example 7

Preparation of N-(4-fluoro-2-methylphenyl)-2H-1,2,3-triazol-4-amine (compound I-36)

Step 1: 1-Benzyl-N-(4-fluoro-2-methylphenyl)-1H-1,2,3-triazol-5-amine

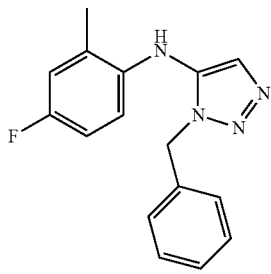

7d

To a mixture of 1-benzyl-1H-1,2,3-triazol-5-amine (235 mg, 1.35 mmol), chloro[2-(di-tert-butylphosphino)-2',4',6'-triisopropyl-1,1'-biphenyl][2-(2-aminoethyl)phenyl)]palladium(II) (9.23 mg, 0.013 mmol), ditert-butyl-[2-(2,4,6-triisopropylphenyl)phenyl]phosphane (5.73 mg, 0.013 mmol) and sodium 2-methylpropan-2-olate (272 mg, 2.83 mmol) under nitrogen was added 1-bromo-4-fluoro-2-methyl-benzene (319 mg, 213.2 µL, 1.69 mmol) and t-BuOH (10 mL) and the reaction heated to reflux for 2 h. The reaction was allowed to cool and concentrated and diluted with water, saturated aqueous ammonium chloride and EtOAc. The aqueous was further extracted with EtOAc and the combined organics dried (Na$_2$SO$_4$) and concentrated. The material was purified by ISCO (0-100% EtOAc in hexanes) to afford the title compound 7d as an oil (247 mg, 65%). MS m/z: 283.2 (M+H)$^+$.

Step 2: N-(4-Fluoro-2-methylphenyl)-2H-1,2,3-triazol-4-amine

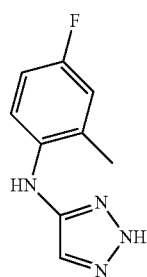

A solution of 1-benzyl-N-(4-fluoro-2-methylphenyl)-1H-1,2,3-triazol-5-amine 7d (247 mg, 0.87 mmol) in EtOAc (8 mL) and MeOH (8 mL) was degassed by vacuum/nitrogen cycles (×3) and treated with palladium on carbon [wet, Degussa] (186 mg, 0.18 mmol). The mixture was degassed by vacuum/hydrogen cycles (×3) and left under a hydrogen atmosphere for 3 h. Reaction was filtered through celite and concentrated and the material purified by FractionLynx to afford the title compound I-36 as a solid (0.5 TFA salt) (121 mg, 55%). $^1$H NMR (500 MHz, d6-DMSO) δ 7.48-7.76 (2H, m), 7.39 (1H, s), 6.99 (1H, dd), 6.91 (1H, dd), 2.25 (3H, t). MS m/z: 193.1 (M+H)$^+$.

The following aminotriazoles were synthesised using a similar procedure as outlined for compound I-36: compounds I-17 and I-23. However, bromide coupling partners were synthesised using the following methodologies.

Synthesis of 2-(2-bromo-5-chlorophenyl)-N-methyl-ethanesulfonamide

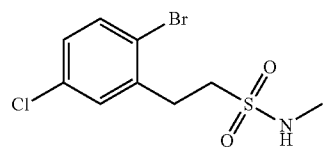

6a

To a solution of methylamine (1.18 mL of 2 M, 2.34 mmol) and triethylamine (477.2 mg, 657 µL, 4.72 mmol) in DCM (20 mL) was added 2-(2-bromo-5-chloro-phenyl)ethanesulfonyl chloride (500 mg, 1.57 mmol) and the mixture stirred at room temperature for 2 h. A further quantity of methylamine (2 mL) was added and the reaction stirred at room temperature for 18 h. The reaction was diluted with DCM and saturated aqueous sodium chloride and the organic layer was concentrated to afford the title compound 6a as an off white solid (465 mg, 95%). $^1$H NMR (500 MHz, d6-DMSO) δ 7.40 (1H, d), 7.16-7.28 (1H, m), 7.04 (1H, dd), 4.51 (1H, brs), 3.18-3.33 (2H, m), 3.05-3.18 (2H, m), 2.75 (3H, s).

Synthesis of tert-butyl 2-bromo-5-chlorobenzyl(methyl)carbamate

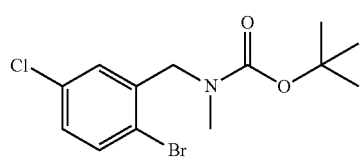

6b

To a solution of 1-(2-bromo-5-chloro-phenyl)-N-methyl-methanamine (1.00 g, 4.26 mmol) in THF (10 mL) was added triethylamine (517.8 mg, 713.2 µL, 5.12 mmol) and tert-butoxycarbonyl tert-butyl carbonate (977.1 mg, 1.029 mL, 4.48 mmol) and the solution stirred at room temperature for 2 h. The reaction was diluted with EtOAc and water and the organic washed with sequentially with 1N HCl, saturated aqueous sodium hydrogen carbonate, and brine. The organic was dried (Na$_2$SO$_4$) and concentrated to afford the title compound 6b as an oil (1.42 g, 100%). $^1$H NMR (500 MHz, d6-DMSO) δ 7.65 (1H, d), 7.29-7.31 (1H, m), 7.18 (1H, s), 4.44 (2H, s), 2.87 (3H, s), 1.41 (9H, s).

Example 8

Preparation of N-(3-fluorophenyl)-2H-1,2,3-triazol-4-amine (compound I-45)

Step 1: N-(3-Fluorophenyl)-2-((2-(trimethylsilyl)ethoxy)methyl)-2H-1,2,3-triazol-4-amine

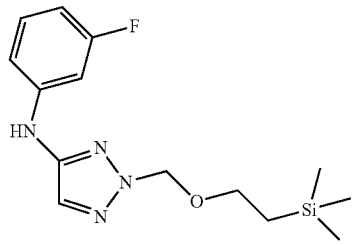

7e

To a mixture of 2-((2-(trimethylsilyl)ethoxy)methyl)-2H-1,2,3-triazol-4-amine 5b (100 mg, 0.47 mmol), chloro[2-(di-tert-butylphosphino)-2',4',6'-triisopropyl-1,1'-biphenyl][2-(2-aminoethyl)phenyl)]palladium(II) (3.21 mg, 0.0047 mmol), di-tert-butyl-[2-(2,4,6-triisopropylphenyl)phenyl]phosphane (1.98 mg, 0.0047 mmol) and sodium-tert-butoxide (94.2 mg, 0.98 mmol) under a nitrogen atmosphere was added 1-bromo-3-fluoro-benzene (81.6 mg, 0.47 mmol) and t-BuOH (4.5 mL). The reaction was heated to reflux for 2 h and allowed to cool and concentrated. The residue was diluted with EtOAc and water and the organic dried (MgSO$_4$) and concentrated. The material was purified by ISCO (0-20% EtOAc in hexanes) to afford the title compound 7e as a colorless oil (51 mg, 35%). MS m/z: 309.2 (M+H)$^+$.

Step 2: N-(3-Fluorophenyl)-2H-1,2,3-triazol-4-amine

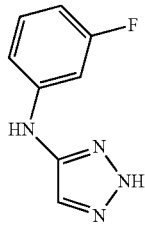 [SMILES: Fc1cccc(Nc2cn[nH]n2)c1]

To N-(3-fluorophenyl)-2-((2-(trimethylsilyl)ethoxy)methyl)-1H-1,2,3-triazol-5-amine 7e (50 mg, 0.16 mmol) was added ethane-1,2-diamine (50 mg, 55.6 µL, 0.83 mmol) and tetrabutylammonium fluoride (424 mg, 478 µL, 1.62 mmol) and the mixture was heated to 90° C. in a microwave for 2 h. The mixture was diluted with EtOAc and water and the organic was washed with water, brine and then dried (MgSO$_4$) and concentrated. Material was purified by Fractionlynx to afford the title compound I-45 as a white solid (10 mg, 35%). $^1$H NMR (500 MHz, d6-DMSO) δ 14.19 (1H, s), 9.02 (1H, s), 7.39 (1H, d), 7.17-7.27 (2H, m), 6.99-7.06 (1H, m), 6.52-6.61 (1H, m). MS m/z: 179.1 (M+H)$^+$.

The following aminotriazoles were synthesised using a similar procedure as outlined for compound I-45: compounds I-4, I-6, I-7, I-8, I-10, I-12, I-15, I-19, I-27, I-38, I-39, I-40, I-41, I-42, I-46, I-47, and I-48. However, bromide coupling partners for compounds I-4, I-6, I-46, I-47, and I-48 were synthesised using the following methodologies.

Synthesis of 1-bromo-4-chloro-2-(methoxymethyl)benzene

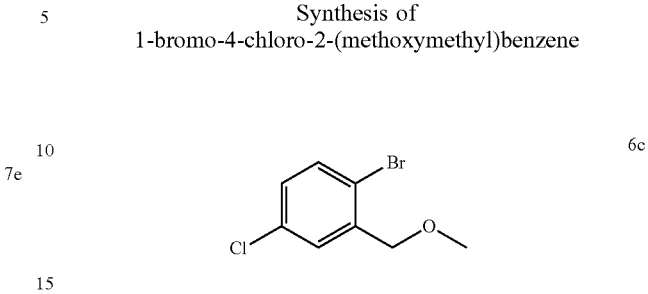

6c

To a solution of (2-bromo-5-chloro-phenyl)methanol (3.16 g, 14.25 mmol) in THF (50 mL) at room temperature was added sodium hydride (684 mg, 17.10 mmol). The mixture was stirred for 30 min and then iodomethane (3.04 g, 1.33 mL, 21.38 mmol) was added and the reaction stirred overnight. The mixture was diluted with saturated aqueous ammonium chloride and EtOAc and the organic washed with water, then brine, and dried (Na$_2$SO$_4$) and concentrated to afford the title compound 6c as an oil (3.36 g, quant). $^1$H NMR (500 MHz, CDCl$_3$) δ 7.40-7.48 (2H, m), 7.11-7.14 (1H, m), 4.47 (2H, s), 3.48 (3H, s).

Synthesis of 1-Bromo-4-chloro-2-(2-methoxyethyl)benzene

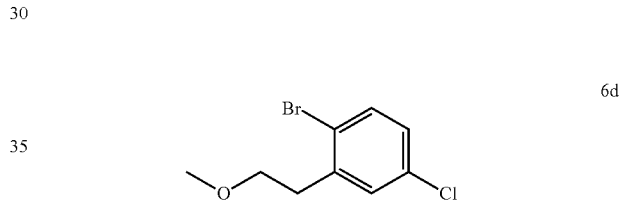

6d

Step 1: 2-(2-bromo-5-chlorophenyl)ethanol

A solution of 2-(2-bromo-5-chloro-phenyl)acetic acid (1.00 g, 4.01 mmol) in THF (16 mL) was cooled to 0° C. Borane-tetrahydrofuran complex (6.0 mL, 62.69 mmol) was added and the solution allowed to warm to room temperature and stirred for 3 h. Another portion of borane-tetrahydrofuran complex (6.0 mL, 62.69 mmol) was added and the reaction stirred overnight. The reaction was cooled to 0° C. and quenched by the careful addition of cold water. The aqueous was extracted with EtOAc and the organic layer washed with 2M HCl, dried (Na$_2$SO$_4$), and concentrated. The material was dissolved in DCM and PS-DEAM (1 g) was added and stirred overnight. The resin was filtered washing with DCM and concentrated to afford 2-(2-bromo-5-chlorophenyl)ethanol as an oil (944 mg, quant). $^1$H NMR (500 MHz, CDCl$_3$) δ 7.40 (1H, d), 7.30 (1H, s), 7.00-7.03 (1H, m), 3.80-3.84 (2H, m), 2.91-2.94 (2H, m).

Step 2: 1-Bromo-4-chloro-2-(2-methoxyethyl)benzene

A solution of 2-(2-bromo-5-chlorophenyl)ethanol (1.00 g, 4.03 mmol) in THF (50 mL) was cooled to −78° C. and LiHMDS (4.24 mL of 1 M, 4.24 mmol) was added the mixture stirred for 40 min. Iodomethane (601 mg, 263.7 µL, 4.24 mmol) was added and the solution allowed to warm to room temperature and stirred for 2 h. The reaction was re-cooled to −78° C. and another portion of LiHMDS (4.24 mL of 1 M, 4.24 mmol) was added, stirred for 40 min, and another portion of iodomethane (601 mg, 263.7 µL, 4.24 mmol) was added. After stirring at room temperature for 2 h the reaction was cooled to 0° C. and quenched with water. The aqueous was extracted with EtOAc and the organics was with brine, dried (Na$_2$SO$_4$), and concentrated. Material was purified using an ISCO (0-100% EtOAc/hexanes) to afford the title compound 6d as a yellow oil (428 mg, 32%). $^1$H NMR (500 MHz, CDCl$_3$) δ 7.39 (1H, d), 7.20 (1H, s), 7.00 (1H, d), 3.54 (2H, t), 3.30 (3H, s), 2.93 (2H, t).

Synthesis of 4-(2-bromo-5-chlorophenethyl)morpholine

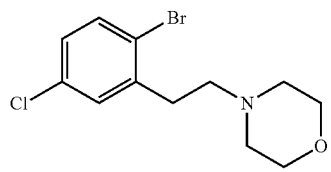

6e

Step 1: 2-bromo-5-chlorophenethyl methanesulfonate

A solution of 2-(2-bromo-5-chloro-phenyl)ethanol (1.65 g, 7.00 mmol) [as prepared in preparation 6] and triethylamine (922 mg, 1.27 mL, 9.11 mmol) in DCM (20 mL) was cooled to 0° C. and methanesulfonyl chloride (883 mg, 597 µL, 7.71 mmol) was added. The mixture was stirred for 2 h and then diluted with DCM and washed sequentially with water and brine, the organic layer dried (MgSO$_4$) and concentrated to afford 2-bromo-5-chlorophenethyl methanesulfonate as a yellow solid (2.11 g, 96%). $^1$H NMR (500 MHz, d6-DMSO) δ 7.67 (1H, d), 7.55 (1H, s), 7.32 (1H, d), 4.44 (2H, t), 3.13-3.36 (5H, m).

Step 2: 4-(2-bromo-5-chlorophenethyl)morpholine

A solution of 2-(2-bromo-5-chloro-phenyl)ethyl methanesulfonate (261 mg, 0.83 mmol) and morpholine (218 mg, 218 µL, 2.50 mmol) in toluene (4 mL) was heated to reflux and stirred overnight. The mixture was allowed to cool to room temperature and diluted with EtOAc and washed sequentially with water and brine, the organic layer dried (MgSO$_4$) and concentrated to afford the title compound 6e as a pale yellow oil (228 mg, 90%). $^1$H NMR (500 MHz, d6-DMSO) δ 7.61 (1H, d), 7.50 (1H, s), 7.24 (1H, D), 3.57-3.59 (4H, m), 2.86 (2H, t), 2.50-2.52 (4H, m), (1×CH$_2$ masked under DMSO peak). MS m/z: 305.9 (M+H)$^+$.

The bromide coupling partner for I-47 was prepared in an analogous fashion to the bromide coupling partner for compound I-46, with the exception that the starting material is ethyl 3-(2-bromo-5-chloro-phenyl)propanoate.

Synthesis of 1-(2-(2-bromo-5-chlorophenoxy)ethyl)-4-methylpiperazine

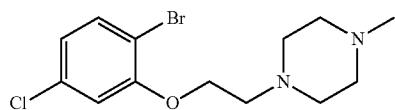

6f

Step 1: 1-bromo-2-(2-bromoethoxy)-4-chlorobenzene

To a suspension of 2-bromo-5-chloro-phenol (2.58 g, 12.44 mmol) in water (8 mL) was added sodium hydroxide (995 mg, 24.88 mmol) and the solution heated to reflux for 1 h and then allowed to cool to room temperature. 1,2-dibromoethane (4.67 g, 24.88 mmol) was added and the mixture heated at reflux for 25 h. The solution was allowed to cool to room temperature and partitioned between EtAOc and water. The aqueous was washed with saturated sodium hydrogen carbonate, water and brine and then dried (MgSO$_4$) and concentrated. Material was purified using an ISCO (0-5% EtOAc/hexanes) to afford 1-bromo-2-(2-bromoethoxy)-4-chlorobenzene as a white solid (1.30 g, 33%). $^1$H NMR (500 MHz, d6-DMSO) δ 7.62 (1H, d), 7.26 (1H, s), 7.02 (1H, d), 4.46 (2H, t), 3.83 (2H, t).

Step 2: 1-(2-(2-bromo-5-chlorophenoxy)ethyl)-4-methylpiperazine

A solution of 1-bromo-2-(2-bromoethoxy)-4-chlorobenzene (200.0 mg, 0.64 mmol) and 1-methylpiperazine (191.1 mg, 1.91 mmol) in toluene (3.0 mL) was heated to reflux for 30 min. The mixture was allowed to cool to room temperature and diluted with EtOAc. The organics were washed with water and brine and then dried (MgSO$_4$) and concentrated to afford the title compound 6f as a pale yellow oil. $^1$H NMR (500 MHz, CDCl$_3$) δ 7.59 (1H, d), 7.26 (1H, s), 6.97 (1H, d), 4.19 (2H, t), 2.72 (2H, t), 2.31 (4H, brs), 2.14 (3H, s).

Example 9

Preparation of 6-chloro-N-(2H-1,2,3-triazol-4-yl)pyridin-3-amine (compound I-22)

Step 1: 6-Chloro-N-(2-((2-(trimethylsilyl)ethoxy)methyl)-2H-1,2,3-triazol-4-yl)pyridin-3-amine

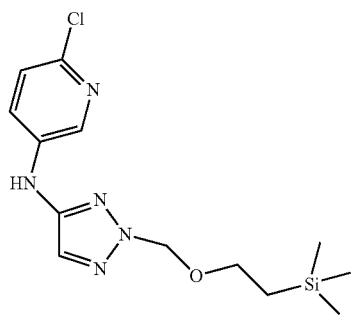

7f

A slurry of 2-((2-(trimethylsilyl)ethoxy)methyl)-2H-1,2,3-triazol-4-amine 5b (130 mg, 0.61 mmol), (6-chloro-3-pyridyl)boronic acid (191 mg, 1.21 mmol), diacetoxycopper (220 mg, 1.21 mmol) and triethylamine (123 mg, 169.0 µL, 1.21 mmol) in DCM (22 mL) was added 4 Å molecular sieves and the mixture stirred overnight at room temperature. The mixture was filtered through celite and treated with aqueous ammonia solution. The organic layer was seperated and washed with brine, dried (Na$_2$SO$_4$), and concentrated to afford the title compound 7f as an oil. MS m/z: 326.1 (M+H)$^+$.

Step 2: 6-Chloro-N-(2H-1,2,3-triazol-4-yl)pyridin-3-amine

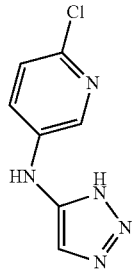 [SMILES: Clc1ccc(Nc2cnn[nH]2)cn1]

A mixture of 6-chloro-N-(2-((2-(trimethylsilyl)ethoxy)methyl)-1H-1,2,3-triazol-5-yl)pyridin-3-amine 7f (175 mg, 0.54 mmol), ethane-1,2-diamine (161 mg, 180 μL, 2.69 mmol) and tetrabutylammonium fluoride (2.69 mL of 2 M in THF, 5.37 mmol) was heated at 90° C. in a microwave for 80 min. The mixture was concentrated and purified by FractionLynx to afford the title compound I-22 as an off white solid (0.25 TFA salt) (32.5 mg, 25%). $^1$H NMR (500 MHz, d6-DMSO) δ 14.28 (1H, s), 9.19 (1H, s), 8.38 (1H, s), 7.82-7.83 (1H, m), 7.42 (1H, s), 7.34-7.36 (1H, m). MS m/z: 196.0 (M+H)$^+$.

The following aminotriazoles were synthesised using a similar procedure as outlined for compound I-22: compound I-43. The boronic acid coupling partner was synthesised using the following methodology.

Synthesis of (4-chloro-2-(2-(N,N-dimethylsulfamoyl)ethyl)phenyl)boronic acid

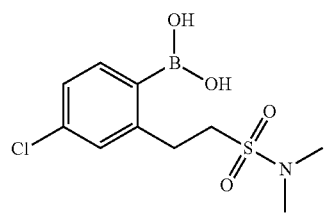

6f

Step 1: 2-(2-bromo-5-chlorophenyl)-N,N-dimethylethanesulfonamide

To a solution of dimethylamine (1.91 mL of 2 M, 3.82 mmol) and triethylamine (386.7 mg, 532.6 μL, 3.82 mmol) in THF (8.1 mL) at room temperature was added 2-(2-bromo-5-chloro-phenyl)ethanesulfonyl chloride (405.0 mg, 1.27 mmol) and the mixture stirred for 10 min. The mixture was diluted with EtOAc and washed subsequently with water and brine, the organic layer dried (MgSO$_4$) and concentrated to afford 2-(2-bromo-5-chlorophenyl)-N,N-dimethylethanesulfonamide as a white solid (413 mg, 99%). $^1$H NMR (500 MHz, d6-DMSO) δ 7.66 (1H, d), 7.60 (1H, s), 7.30 (1H, d), 3.31-3.34 (2H, m), 3.08-3.12 (2H, m).

Step 2: 2-(5-chloro-2-(4,4,5,5-tetramethyl-1,3,2-dioxaborolan-2-yl)phenyl)-N,N-dimethylethane sulfonamide A mixture of 2-(2-bromo-5-chlorophenyl)-N,N-dimethylethanesulfonamide (413 mg, 1.26 mmol), potassium acetate (521 mg, 5.31 mmol) and bis(pinacolato)diboron (369 mg, 1.45 mmol) in dioxane (11.8 mL) was degassed via vacuum/nitrogen cycles (×3) and then 1-cyclopenta-1,4-dienyl-diphenyl-phosphane-dichloromethane-dichloropalladium-iron (82.6 mg, 0.10 mmol) was added and the reaction heated at 95° C. overnight. The reaction was allowed to cool to room temperature and diluted with EtOAc and water. The organic was washed with brine, dried (MgSO$_4$) and concentrated. Material was purified by ISCO (0-20% EtOAc/hexanes) to afford 2-(5-chloro-2-(4,4,5,5-tetramethyl-1,3,2-dioxaborolan-2-yl)phenyl)-N,N-dimethylethane sulfonamide as a white solid (357 mg, 76%). MS m/z: 374.2 (M+H)$^+$.

Step 3: (4-chloro-2-(2-(N,N-dimethylsulfamoyl)ethyl)phenyl)boronic acid

To a solution of 2-(5-chloro-2-(4,4,5,5-tetramethyl-1,3,2-dioxaborolan-2-yl)phenyl)-N,N-dimethylethanesulfonamide (357 mg, 0.96 mmol) in THF (14 mL) and water (3.5 mL) was added sodium(meta)periodate (284 mg, 2.87 mmol) and the mixture stirred at room temperature for 15 min. HCl (1.91 mL of 2 M, 3.82 mmol) was added and the mixture stirred for a further 4.5 h. The reaction was extracted with EtOAc and the organic washed sequentially with water and brine, dried (MgSO$_4$) and concentrated to afford the title 6f compound as a cream sticky solid (265 mg, 95%). MS m/z: 292.1 (M+H)$^+$.

Example 10

Preparation of 3-(2-((2H-1,2,3-triazol-4-yl)amino)-5-chlorobenzyl)cyclobutanecarboxylic acid (compound I-28)

Step 1: Ethyl-3-[(2-bromo-5-chloro-phenyl)methylene]cyclobutanecarboxylate

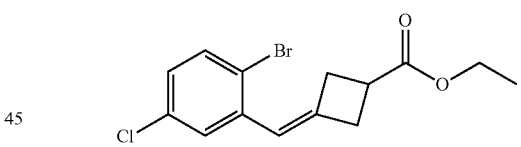

6g

Preparation of (2-Bromo-5-chloro-phenyl)methyl-triphenyl-phosphonium bromide: To a solution of 1-bromo-2-(bromomethyl)-4-chloro-benzene (3.00 g, 10.55 mmol) in THF (50 mL) was added triphenylphosphane (4.15 g, 15.82 mmol) and the solution was stirred at room temperature for 20 h. During this time a white solid precipitated. Reaction mixture was filtered to give a white solid, which was slurried with ether and filtered to afford the title compound as a white solid (3.74 g, 65%). MS m/z: 467.0 (M+H)$^+$.

Preparation of Ethyl-3-[(2-bromo-5-chlorophenyl)methylene]cyclobutanecarboxylate: Sodium hydride (85 mg, 2.11 mmol) was added in small portions to a solution of (2-bromo-5-chloro-phenyl)methyl-triphenyl-phosphonium bromide (1.05 g, 1.92 mmol) in THF (8 mL) and the solution stirred at room temperature for 2 h. A solution of ethyl 3-oxocyclobutanecarboxylate (273 mg, 1.92 mmol) in THF (1 mL) was added and the solution stirred at room temperature for 24 h. Water and EtOAc was added and the organic washed with brine, dried (MgSO$_4$) and concentrated. Material was purified by flash column chromatography on silica gel eluting with 5% ether in hexanes to afford the title compound 6g as a semi solid/oil (63 mg, 10%). ¹H NMR (500 MHz, CDCl₃) δ 7.37-7.40 (1H, d), 7.15 (1H, s), 7.91-7.95 (1H, d), 6.32 (1H, s), 4.11 (2H, q), 3.00-3.27 (5H, m), 1.18 (3H, t).

Step 2: 3-(2-((1-Benzyl-1H-1,2,3-triazol-5-yl)amino)-5-chlorobenzylidene)cyclobutane carboxylic acid

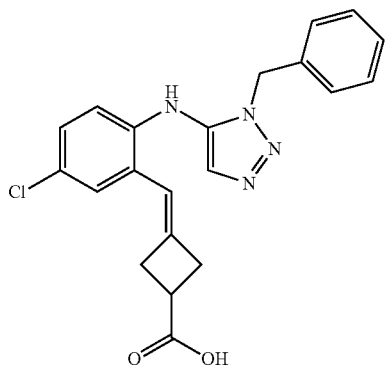

7g

To a mixture of 1-benzyl-1H-1,2,3-triazol-5-amine 5a (43.2 mg, 0.25 mmol), chloro[2-(di-tert-butylphosphino)-2',4',6'-triisopropyl-1,1'-biphenyl][2-(2-aminoethyl)phenyl)]palladium(II) (1.71 mg, 0.0025 mmol), 2-di-tert-butylphosphino-2',4',6'-triisopropylbiphenyl (1.1 mg, 0.0025 mmol) and sodium tert-butoxide (50 mg, 0.52 mmol) under a nitrogen atmosphere was added ethyl-3-[(2-bromo-5-chloro-phenyl)methylene]cyclobutanecarboxylate 6g (90 mg, 0.27 mmol) and t-BuOH (2 mL). The mixture was degassed by vacuum/nitrogen cycles (3×) and then heated to reflux for 1 h. The mixture was concentrated and the resulting residue was treated with water, acidified with 5% citric acid, and extracted with EtOAc (3×). The combined organic layers were washed with brine, dried (MgSO₄), and concentrated to afford the title compound 7g as a brown viscous oil (75 mg, 76%). MS m/z: 395.2 (M+H)⁺.

Step 4: 3-(2-((2H-1,2,3-Triazol-4-yl)amino)-5-chlorobenzyl) cyclobutanecarboxylic acid

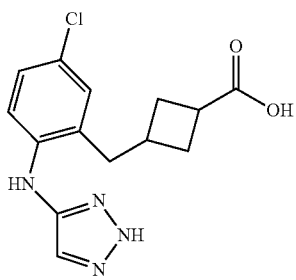 [SMILES: O=C(O)C1CC(Cc2cc(Cl)ccc2Nc2cn[nH]n2)C1]

To a solution of 3-(2-((1-benzyl-1H-1,2,3-triazol-5-yl)amino)-5-chlorobenzylidene)cyclobutanecarboxylic acid 7g (75 mg, 0.19 mmol) and dibromozine (17.1 mg, 0.076 mmol) in EtOAc (2 mL) and MeOH (2 mL) was added 10% Pd on C [wet Degussa type] (40 mg, 0.038 mmol). The reaction was then flushed with hydrogen via vacuum/hydrogen cycles (3×) and the mixture stirred under a hydrogen atmosphere for 2 h at room temperature. Additional 10% Pd on C [wet Degussa type] (40 mg, 0.038 mmol) was added and stirred under hydrogen for a further 1 h. Acetic acid (23 mg, 21.60 µL, 0.38 mmol) was then added and mixture stirred under hydrogen overnight. Additional acetic acid (22 mg, 21.60 µL, 0.38 mmol) was added and stirred under hydrogen atmosphere again overnight. The reaction mixture was then filtered through celite washing through with methanol. The filtrate was concentrated and the material purified by FractionLynx to afford the title compound I-28 as a white solid (1.5 TFA salt) (4.0 mg, 3.9% yield). ¹H NMR (500 MHz, d6-DMSO) δ 7.78 (1H, brs), 7.59 (1H, brs), 7.46 (1H, brs), 7.10-7.12 (1H, m), 7.06 (1H, d), 2.87-2.94 (1H, m), 2.72 (2H, d), 2.50-2.55 (1H, masked signal), 2.18-2.25 (2H, m), 1.84-1.90 (2H, m). MS m/z: 307.1 (M+H)⁺.

Example 11

Preparation of 3-(2-((2H-1,2,3-triazol-4-yl)amino)-5-chlorophenyl)-2,2-dimethylpropanoic acid (compound I-33)

Step 1: Ethyl 3-(2-bromo-5-chloro-phenyl)-2,2-dimethyl-propanoate

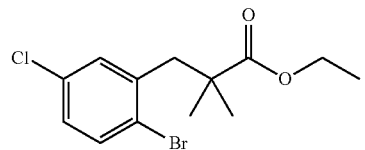

6h

To a solution of diisopropylamine (818 mg, 1.13 mL, 8.09 mmol) in THF (20 mL) cooled to −78° C. was added n-butyllithium (3.10 mL of 2.5 M in hexanes, 7.74 mmol) over 5 min keeping temp below −70° C. On complete addition the mixture was allowed to warm to 0° C. then cooled back to −78° C. Ethyl 2-methylpropanoate (817 mg, 940 µL, 7.03 mmol) was added and the mixture stirred at below −70° C. for 45 min. A solution of 1-bromo-2-(bromomethyl)-4-chloro-benzene (2.00 g, 7.03 mmol) in THF (10 mL) was added and the reaction allowed to warm slowly to room temperature overnight. The mixture was quenched with saturated aqueous ammonium chloride solution and extracted with EtOAc (3×). The combined organics were washed sequentially with water (3×) and brine (1×), dried (MgSO₄), and concentrated. Material was purified by flash column chromatography eluting with 2.5% ether in hexanes to afford the title compound 6h as a colourless oil (747 mg, 32%). ¹H NMR (500 MHz, d6-DMSO) δ 7.63-7.65 (1H, m), 7.25-7.28 (2H, m), 4.09 (2 h, q), 3.04 (2H, s), 1.17-1.20 (9H, m).

Step 2: 3-(2-((1-Benzyl-1H-1,2,3-triazol-5-yl)amino)-5-chlorophenyl)propanoic acid Step 3: 3-(2-((2H-1,2,3-Triazol-4-yl)amino)-5-chlorophenyl)-2,2-dimethylpropanoic acid

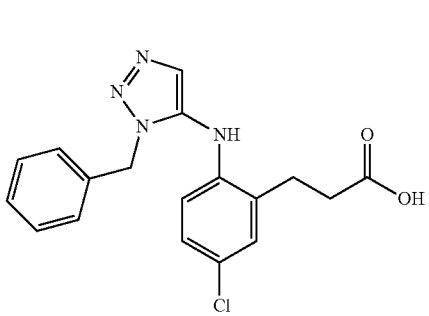

7h

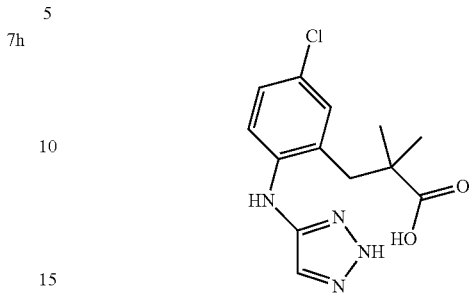

To a mixture of 1-benzyl-1H-1,2,3-triazol-5-amine 5a (100 mg, 0.57 mmol), chloro[2-(di-tert-butylphosphino)-2',4',6'-triisopropyl-1,1'-biphenyl][2-(2-aminoethyl)phenyl)]palladium(II) (4.0 mg, 0.0057 mmol), 2-di-tert-butylphosphino-2',4',6'-triisopropylbiphenyl (2.4 mg, 0.0057 mmol) and sodium tert-butoxide (116 mg, 1.21 mmol) under a nitrogen atmosphere was added ethyl 3-(2-bromo-5-chlorophenyl)-2,2-dimethyl-propanoate 6h (220 mg, 0.69 mmol) and t-BuOH (4.5 mL). The reaction mixture was degassed by vacuum/nitrogen cycles (3×) and then heated to reflux for 1 h. The reaction mixture was concentrated and the residue was treated with water, acidified with 5% citric acid and extracted with EtOAc (3×). The combined organics were washed with brine (2×), dried (MgSO$_4$), and concentrated. Material was purified by ISCO (0-50% EtOAc/hexanes) to afford the title 7h compound as an orange foam (85 mg, 39%). MS m/z: 385.2 (M+H)$^+$.

To a solution of 3-(2-((1-benzyl-1H-1,2,3-triazol-5-yl)amino)-5-chlorophenyl)propanoic acid 7h (85 mg, 0.22 mmol) in toluene (3.5 mL) was added aluminium trichloride (165 mg, 1.24 mmol) and the mixture heated at 100° C. for 1 h. The mixture was allowed to cool to room temperature and diluted with water and EtOAc followed by 5% citric acid solution. The aqueous was further extracted with EtOAc and the combined organics washed with brine, dried (MgSO$_4$), and concentrated. Material was purified by ISCO (0-60% EtOAc/hexanes) to afford the title compound I-33 as an off white solid (36 mg, 38%). $^1$H NMR (500 MHz, d6-DMSO) δ 14.14 (1H, brs), 12.37 (1H, brs), 7.84 (1H, brs), 7.60-7.63 (1H, m), 7.38-7.41 (1H, m), 7.14 (1H, d), 7.08 (1H, d), 2.77 (1H, d), 2.67 (1H, d), 1.12 (6H, s). MS m/z: 295.1 (M+H)$^+$.

The following aminotriazoles were synthesised using a similar procedure as outlined for compound I-33: Compounds I-31, I-32, and I-35

| | | Analytical Data | |
|---|---|---|---|
| Cmpd No. | LCMS ES+ | LCMS (Rt min) | HNMR |
| I-1 | 223.0 | 0.82 | 1H NMR (500 MHz, DMSO) δ 7.78 (br s, 1H), 7.59 (br s, 1H), 7.47 (s, 1H), 7.14-7.10 (m, 2H), 2.65 (q, J = 7.5 Hz, 2H), 1.17 (t, J = 7.5 Hz, 3H). |
| I-2 | 195.0 | 0.69 | 1H NMR (500 MHz, DMSO) δ 14.17 (s, 1H), 8.93 (s, 1H), 7.39-7.30 (m, 3H), 7.25 (d, J = 8.4 Hz, 2H). |
| I-3 | 240.9 | 0.71 | 1H NMR (500 MHz, DMSO) δ 8.79 (s, 1H), 7.42-7.24 (m, 3H), 7.26-7.16 (m, 2H). |
| I-4 | 239.0 | 0.74 | 1H NMR (500 MHz, DMSO) δ 14.35 (brs, 1H), 7.72 (s, 1H), 7.62-7.55 (m, 1H), 7.56-7.49 (m, 1H), 7.33-7.19 (m, 2H), 5.76 (s, 2H), 4.50 (s, 3H). |
| I-5 | 209.0 | 0.76 | 1H NMR (500 MHz, DMSO) δ 7.42 (d, 1H), 7.37 (s, 1H), 7.29 (s, 1H), 7.10 (d, 1H), 7.05 (dd, 1H), 2.22 (s, 3H) |
| I-6 | 253.1 | 0.77 | 1H NMR (500 MHz, DMSO) δ 14.1-13.94 (br s, 1H), 7.86 (s, 1H) 7.62-7.44 (m, 2H), 7.17-7.13 (m, 2H), 3.58-3.55(m, 2H), 3.28(s, 3H), 2.90-2.88 (m, 2H). |
| I-7 | 223.1 | 0.82 | 1H NMR (500 MHz, DMSO-d6) δ 8.79 (s, 1H), 7.42 (s, 1H), 7.26-7.20 (m, 2H), 7.15-7.11 (m, 1H), 2.64 (q, J = 7.5 Hz, 2H), 1.17 (t, J = 7.5 Hz, 3H). |
| I-8 | 225.0 | 0.68 | 1H NMR (500 MHz, DMSO) δ 8.67 (s, 1H) 7.30 (s, 1H) 7.20 (d, 1H), 7.10 (s, 1H) 6.75 (d, 1H), 3.72(s, 3H). |
| I-9 | 225.1 | 0.59 | 1H NMR (500 MHz, DMSO) δ 14.20 (s, 1H), 7.85-7.80 (s, 1H), 7.60 (s, 1H), 7.51 (s, 1H), 7.31 (d, J = 2.6 Hz, 1H), 7.19 (dd, J = 8.7, 2.7 Hz, 1H), 4.55 (s, 2H). |
| I-10 | 324.0 | 0.72 | 1H NMR (500 MHz, DMSO) δ 14.23 (brs, 1H), 7.81 (s, 1H), 7.71 (d, J = 8.7 Hz, 1H), 7.52 (s, 1H), 7.09 (d, J = 2.4 Hz, 1H), 6.92 (dd, J = 8.6, |

-continued

Analytical Data

| Cmpd No. | LCMS ES+ | LCMS (Rt min) | HNMR |
|---|---|---|---|
| | | | 2.3 Hz, 1H), 4.20 (t, J = 5.9 Hz, 2H), 3.62-3.56 (m, 4H), 3.42-3.24 (m, 4H), 2.77 (t, J = 5.9 Hz, 2H). |
| I-11 | 195.0 | 0.69 | 1H NMR (500 MHz, DMSO) δ 8.66 (s, 1H), 7.34-7.21 (m, 2H), 7.18-7.16 (m, 1H), 7.06 (d, 1H), 6.69 (d, 1H). |
| I-12 | 225.1 | 0.76 | 1H NMR (500 MHz, DMSO) δ 7.67 (d, J = 8.7 Hz, 1H), 7.61 (br s, 1H), 7.33 (s, 1H), 6.96 (d, J = 2.3 Hz, 1H), 6.87 (dd, J = 8.6, 2.3 Hz, 1H), 3.88 (s, 3H). |
| I-13 | 213.0 | 0.71 | 1H NMR (500 MHz, DMSO) δ 8.74 (s, 1H), 7.50 (dd, 1H), 7.31 (s, 1H), 7.23 (dd, 1H), 7.13-7.10 (m, 1h) |
| I-14 | 213.0 | 0.72 | 1H NMR (500 MHz, DMSO) δ 9.07 (s, 1H), 7.40 (s, 1H), 7.36-7.32 (m, 2H), 7.02 (dd, 1H) |
| I-15 | 223.1 | 0.78 | 1H NMR (500 MHz, DMSO) δ 7.26-7.25 (br m, 1H), 7.11 (br s, 2H), 6.85 (br m, 1H), 3.18 (s, 1H), 2.12 (s, 6H). |
| I-16 | 229.0 | 0.85 | 1H NMR (500 MHz, DMSO) δ 9.20 (s, 1H), 7.48-7.45 (m, 1H), 7.44-7.25 (m, 2H), 6.91 (s, 1H). |
| I-17 | 316.0 | 0.65 | 1H NMR (500 MHz, MeOD) δ 7.41 (s, 2H), 7.25 (d, J = 2.5 Hz, 1H), 7.16 (dd, J = 8.7, 2.5 Hz, 1H), 3.39-3.32 (m, 2H), 3.15-3.08 (m, 2H), 2.70 (s, 3H). |
| I-18 | 259.0 | 0.73 | 1H NMR (500 MHz, DMSO) δ 14.18 (s, 1H), 8.96 (d, J = 7.1 Hz, 1H), 7.71 (s, 1H), 7.36 (s, 1H), 7.24 (d, J = 6.7 Hz, 2H). |
| I-19 | 229.0 | 0.78 | 1H NMR (500 MHz, DMSO) δ 13.79 (brs, 1H), 9.14 (s, 1H), 7.63 (1H, s), 7.44-7.42 (m, 2H), 7.21 (d, 1H) |
| I-20 | 266.1 | 0.62 | 1H NMR (500 MHz, DMSO) δ 8.53 (t, J = 6.1 Hz, 1H), 8.36-8.32 (m, 1H), 7.61 (d, J = 8.6 Hz, 1H), 7.44 (s, 1H), 7.25-7.15 (m, 2H), 4.28 (d, J = 6.2 Hz, 2H), 1.93 (s, 3H). |
| I-21 | 302.1 | 0.62 | 1H NMR (500 MHz, DMSO) δ 7.77 (s, 1H), 7.54 (d, J = 8.7 Hz, 1H), 7.47 (s, 1H), 7.33 (d, J = 2.6 Hz, 1H), 7.23 (dd, J = 8.7, 2.6 Hz, 1H), 4.21 (s, 2H), 2.97 (s, 3H). |
| I-22 | 196.0 | 0.49 | 1H NMR (500 MHz, DMSO) δ 14.28 (s, 1H), 9.19 (s, 1H), 8.38 (s, 1H), 8.83 (d, 1H), 7.42 (s, 1H), 7.35 (d, 1H). |
| I-23 | 338.0 | 0.96 | 1H NMR (500 MHz, DMSO) δ 8.16 (s, 1H), 7.63 (s, 1H), 7.40 (s, 1H), 7.23 (d, J = 8.5 Hz, 1H), 7.16 (s, 1H), 4.41 (s, 2H), 2.80 (s, 3H), 1.47-1.36 (m, 9H). |
| I-24 | 179.0 | 0.6 | 1H NMR (500 MHz, DMSO) δ 8.28 (brs, 1H), 7.20 (s, 1H), 7.18-7.14 (m, 2H), 7.01-6.96 (m, 2H). |
| I-25 | 321.0 | 0.81 | 1H NMR (500 MHz, CDCl3) δ 7.76 (d, 1H), 7.50 (s, 1H), 7.44 (d, 1H), 7.29 (s, 1H), 7.26 (dd, 1H). |
| I-26 | 265.9 | 0.59 | 1H NMR (500 MHz, DMSO) δ 15.58 (brs, 1H), 8.56 (s, 1H), 8.07 (d, 1H), 7.79-7.68 (m, 3H). |
| I-27 | 229.1 | 0.78 | 1H NMR (500 MHz, DMSO) δ 8.22 (br s, 1H), 7.81-7.79 (m, 1H), 7.58 (s, 1H), 7.51 (d, J = 2.5 Hz, 1H), 7.29 (dd, J = 8.9, 2.5 Hz, 1H). |
| I-28 | 307.1 | 0.50 | 1H NMR (500 MHz, DMSO) δ 7.78 (br s, 1H), 7.59 (br s, 1H), 7.46 (br s, 1H), 7.12-7.10 (m, 1H), 7.06 (d, J = 2.6 Hz, 1H), 2.94-2.87 (m, 1H), 2.72 (d, J = 7.3 Hz, 2H), 2.55-2.50 (1H, masked signal), 2.25-2.18 (m, 2H), 1.90-1.84 (m, 2H). |
| I-29 | 195.0 | 0.67 | 1H NMR (500 MHz, DMSO) δ 8.05 (s, 1H), 7.79 (1H, d), 7.59 (s, 1H), 7.40 (d, J = 8.5 Hz, 1H), 7.24-7.21 (m, 1H), 6.84-6.80 (m, 1H). |
| I-30 | 213.0 | 0.72 | 1H NMR (500 MHz, DMSO) δ 14.24 (brs, 1H), 8.71 (s, 1H), 9.94 (s, 1H), 7.45 (s, 1H), 7.35 (d, 1H), 7.18 (d, 1H). |
| I-31 | 267.0 | 0.45 | 1H NMR (500 MHz, DMSO) δ 14.18 (s, 1H), 12.18 (s, 1H), 7.96 (s, 1H), 7.74-7.35 (m, 2H), 7.20-7.00 (m, 2H), 2.87 (t, J = 7.6 Hz, 2H), 2.56 (d, J = 12.4 Hz, 2H). |
| I-32 | 309.1 | 0.56 | 1H NMR (500 MHz, DMSO) δ 14.21 (br s, 1H), 12.16 (br s, 1H), 7.77 (br s, 1H), 7.49-7.43 (br m, 2H), 7.13-7.09 (m, 2H), 2.83-2.81 (m, 2H), 1.92 (sextet, J = 13.3, 6.7 Hz, 1H), 1.25 (br s, 1H), 0.98 (dd, J = 13.7, 6.8 Hz, 6H). |
| I-33 | 295.1 | 0.61 | 1H NMR (500 MHz, DMSO) δ 14.14 (br s, 1H), 12.37 (br s, 1H), 7.84 (br s, 1H), 7.63-7.60 (br m, 1H), 7.41-7.38 (br m, 1H), 7.14 (d, J = 8.3 Hz, 1H), 7.08 (d, J = 2.6 Hz, 1H), 2.77 (d, J = 15.4 Hz, 1H), 2.67 (d, J = 15.4 Hz, 1H), 1.12 (s, 6H). |

-continued

Analytical Data

| Cmpd No. | LCMS ES+ | LCMS (Rt min) | HNMR |
|---|---|---|---|
| I-34 | 224.1 | 0.57 | 1H NMR (500 MHz, DMSO) δ 8.46 (brs, 4H), 7.64 (d, 1H), 7.53 (s, 1H), 7.48 (d, 1H), 7.32 (dd, 1H), 4.14-4.10 (m, 2H). |
| I-35 | 323.2 | 0.59 | 1H NMR (500 MHz, DMSO) δ 14.18 (br s, 1H), 12.12 (br s, 1H), 7.65 (br s, 1H), 7.50-7.37 (br m, 2H), 7.14-7.10 (m, 2H), 2.88 (d, J = 14.7 Hz, 1H), 2.80-2.75 (m, 1H), 2.47-2.46 (m, 1H), 1.03 (s, 9H). |
| I-36 | 193.0 | 0.68 | 1H NMR (500 MHz, DMSO) δ 7.76-7.48(m, 2H), 7.39 (s, 1H), 6.99 (ddd, J = 9.5, 3.1, 0.9 Hz, 1H), 6.91 (dddd, J = 9.0, 8.4, 3.1, 0.7 Hz, 1H), 2.25 (t, J = 0.6 Hz, 3H). |
| I-37 | 241.0 | 0.77 | 1H NMR (500 MHz, DMSO) δ 14.20 (brs, 1H), 8.95 (s, 1H), 7.58 (s, 1H), 7.42 (d, 1H), 7.20-7.15 (m, 2H), 6.93 (d, 1H). |
| I-38 | 209.0 | 0.79 | 1H NMR (500 MHz, DMSO-d6) δ 14.13 (s, 1H), 9.00-8.52 (m, 1H), 7.70-6.70 (m, 3H), 2.28 (s, 3H). |
| I-39 | 209.0 | 0.75 | 1H NMR (500 MHz, DMSO-d6) δ 14.19 (s, 1H), 7.87 (s, 1H), 7.47 (m, 2H), 7.08 (t, J = 8.1 Hz, 1H), 6.96-6.81 (m, 1H), 2.31 (s, 3H). |
| I-40 | 221.1 | 0.81 | 1H NMR (500 MHz, DMSO) δ 14.17 (s, 1H), 8.16 (s, 1H), 7.65 (s, 1H), 7.47 (d, J = 2.5 Hz, 1H), 7.5 (s, 1H), 7.22 (m, J = 7.5 Hz, 1H), 7.05 (dd, J = 17.2, 11.0, Hz, 1H) 5.80 (dd, J = 17.2, 1.2 Hz, 1H), 5.36 (dd, J = 10.9, 1.2 Hz, 1H). |
| I-41 | 209.0 | 0.76 | 1H NMR (500 MHz, DMSO-d6) δ 14.23 (s, 1H), 8.92 (s, 1H), 7.45 (s, 1H), 7.27 (s, 1H), 7.01 (s, 1H), 6.68 (s, 1H), 2.29 (m, 3H). |
| I-42 | 209.1 | 0.79 | 1H NMR (500 MHz, DMSO-d6) δ 14.21 (s, 1H), 7.93 (s, 1H), 7.79 (s, 1H), 7.50 (s, 1H), 7.11 (m, 1H), 6.87-6.54 (m, 1H), 2.24 (s, 3H). |
| I-43 | 330.1 | 0.75 | 1H NMR (500 MHz, DMSO) δ 7.93 (br s, 1H), 7.48 (br s, 1H), 7.43 (br s, 1H), 7.27 (d, J = 2.5 Hz, 1H), 7.18 (dd, J = 8.7, 2.6 Hz, 1H), 3.37-3.34 (m, 2H), 3.06-3.02 (m, 2H), 2.80 (s, 6H). |
| I-44 | 220.0 | 0.68 | 1H NMR (500 MHz, DMSO-d6) δ 14.45 (s, 1H), 9.33 (s, 1H), 7.80 (s, 1H), 7.65-7.39 (m, 3H). |
| I-45 | 179.1 | 0.63 | 1H NMR (500 MHz, DMSO-d6) δ 14.19 (s, 1H), 9.02 (s, 1H), 7.39 (d, J = 1.9 Hz, 1H), 7.27-7.17 (m, 2H), 7.06-6.99 (m, 1H), 6.61-6.52 (m, 1H). |
| I-46 | 308.1 | 0.78 | 1H NMR (500 MHz, DMSO) δ 14.29 (br s, 1H), 9.93 (br s, 1H), 7.89 (br s, 1H), 7.50 (br s, 2H), 7.26 (d, J = 2.5 Hz, 1H), 7.22 (dd, J = 8.7, 2.6 Hz, 1H), 4.05 (d, J = 12 Hz, 2H), 3.75-3.66 (masked signal, 2H), 3.53 (d, J = 12 Hz, 2H), 3.38 (t, J = 8.2 Hz, 2H), 3.17-3.15 (m, 2H), 3.08-3.05 (m, 2H). |
| I-47 | 322.1 | 0.79 | 1H NMR (500 MHz, DMSO) δ 10.22 (br s, 1H), 7.88 (br s, 1H), 7.55 (d, J = 8.8 Hz, 1H), 7.49 (s, 1H), 7.20 (d, J = 2.6 Hz, 1H), 7.15 (dd, J = 8.7, 2.6 Hz, 1H), 3.98 (d, J = 11.5 Hz, 2H), 3.67 (t, J = 12.2 Hz, 2H), 3.46 (d, J = 12.2 Hz, 2H), 3.19-3.15 (m, 2H), 3.11-3.04 (m, 2H), 2.71 (t, J = 7.8 Hz, 2H), 1.99-1.93 (m, 2H). |
| I-48 | 339.1 | 0.68 | 1H NMR (500 MHz, DMSO) δ 7.86 (br s, 1H), 7.69 (br s, 1H), 7.55 (br s, 1H), 7.10 (d, J = 2.3 Hz, 1H), 6.95 (dd, J = 8.7, 2.3 Hz, 1H), 4.31 (t, J = 5.0 Hz, 2H), 3.69-2.95 (masked signals, 6H), 2.81 (s, 3H), 2.53-2.50 (masked signal, 4H). |

IDO1 Assay

The compounds of the present invention are evaluated as inhibitors of IDO1 using the following assay.

Example 12

Cellular IDO1 Inhibition Assay

Compounds can be screened for their ability to inhibit intracellular IDO1 activity, by measuring the production of L-kynurenine by HeLa cells in which IDO1 expression is induced by IFN-γ. L-Kynurenine levels can be determined by chemical conversion of L-kynurenine with Ehrlich's reagent (Yue et. al., J Med Chem 2009 Dec. 10; 52(23): 7364-7).

HeLa cells were plated at 20,000 cells per well in 96-well culture plates (Costar 3598) in DMEM (Sigma D5671) supplemented with 10% fetal bovine serum (SAFC Biosciences 12003C), Penicillin/Streptomycin solution diluted 1:100 (Sigma P7539), 4 mM L-glutamine (Sigma G7513), 1% Non Essential Aminoacids (Sigma M7145) and 1 mM Sodium Pyruvate (Sigma S8636). Cells were allowed to adhere for 24 hours at 37° C. in 5% $CO_2$. Subsequently compounds were first serially diluted ⅓ in DMSO then further diluted in media and finally added to the cells, giving a maximal final concentration of 40 µM. Additional medium containing L-tryptophan to a final concentration of 250 µM (Sigma T0254) and human recombinant IFN-γ (R&D Systems 285-IF) were added to the wells to stimulate IDO1 production. Cells were incubated at 37° C. in 5% $CO_2$ for 48 hours.

For the measurement of L-kynurenine in HeLa supernatants, plates were centrifuged at 1000 RPM for 5 minutes and 140 µl of media transferred into a polypropylene 96 well plate (Costar 3879) containing 10 µl of 26% Trichloroacetic Acid in water (Sigma T9159). Plates were then sealed using a plate sealer (PlateLoc, Agilent Technology) and incubated at 50° C. for 30 minutes. Plates were centrifuged at 2400 RPM for 10 minutes and 100 µl of media transferred to polystyrene 96-well plates together with 100 µl of Ehrlich's reagent (2% p-Dimethylaminobenzaldehyde, (Sigma D2004) in acetic acid (Fisher, A/400/PB17)). Following the addition of Ehrlich's reagent the absorbance at 490 nm was read using a spectrophotometer (Spectramax Plus, Molecular Devices). Kynurenine levels were plotted against compound concentrations to generate dose response curves and obtain IC50 values for each active compound using Genedata Screener® Software.

Cellular IC50 values for each compound may be found in Table 2, below, wherein A=<0.1 µM; B=0.1 µM–1 µM; and C=1 µM–40 µM.

TABLE 2

| Cmpd No. | Cellular Assay IC50 Values (µM) |
| --- | --- |
| I-1 | A |
| I-2 | A |
| I-3 | A |
| I-4 | A |
| I-5 | A |
| I-6 | A |
| I-7 | B |
| I-8 | B |
| I-9 | B |
| I-10 | B |
| I-11 | B |
| I-12 | B |
| I-13 | B |
| I-14 | B |
| I-15 | B |
| I-16 | B |
| I-17 | B |
| I-18 | B |
| I-19 | B |
| I-20 | B |
| I-21 | C |
| I-22 | C |
| I-23 | C |
| I-24 | B |
| I-25 | C |
| I-26 | — |
| I-27 | C |
| I-28 | C |
| I-29 | C |
| I-30 | C |
| I-31 | C |
| I-32 | C |
| I-33 | C |
| I-34 | C |
| I-35 | C |
| I-36 | A |
| I-37 | B |
| I-38 | B |
| I-39 | B |
| I-40 | A |
| I-41 | B |
| I-42 | A |
| I-43 | B |
| I-44 | B |
| I-45 | B |
| I-46 | B |
| I-47 | B |
| I-48 | B |

Example 13

Cellular Viability Assay

To ensure that reduction in IDO1 activity was not caused by non-specific cytotoxicity of a given compound, cell viability of stimulated HeLa cells after incubation with compound was assessed by measuring mitochondrial function using 3-(4,5-dimethylthiazol-2-yl)-5-(3-carboxymethoxyphenyl)-2-(4-sulfophenyl)-2H-tetrazolium, inner salt assay (MTS; Promega G3581). For the MTS viability assay 5,000 HeLa cells per well were seeded and treated as described in example 12. After 48 hour incubation, cell plates were removed from the 37° C. incubator and 40 µl of Cell Titer 96 Aqueous solution (Promega, G358B) added to each well. Cells were incubated for 1 hour at 37° C. in 5% $CO_2$ and absorbance read at 490 nm in the spectrophotometer. Absorbance values were plotted against compound concentrations to generate dose response curves and obtain IC50 values for each compound using Genedata Screener® Software.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound of formula I-A:

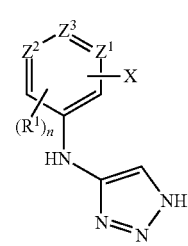

I-A or a pharmaceutically acceptable salt thereof, wherein:
n is 0-4;
X is halo;
$Z^1$, $Z^2$, and $Z^3$ are CH or N, wherein CH is optionally substituted with $R^1$ or X;
$R^1$ is independently selected from halo; —CN; $Q^X$; or a $C_{1-10}$aliphatic chain wherein up to four methylene units of the aliphatic chain are optionally replaced with —O—, —NR—, —S—, —C(O)—, S(O)—, or —S(O)$_2$—; $R^1$ is optionally substituted with 0-5 $J^1$ groups;
$Q^X$ is a 3-7 membered monocyclic fully saturated, partially unsaturated, or aromatic ring containing 0-3 heteroatoms independently selected from nitrogen, oxygen, or sulfur;

$J^1$ is independently selected from halo; —CN; $Q^Y$; or a $C_{1-6}$aliphatic chain wherein up to three methylene units of the aliphatic chain are optionally replaced with —O—, —NR—, —S—, —C(O)—, S(O)—, or —S(O)$_2$—; $J^1$ is optionally substituted with 0-5 $J^2$ groups; or two occurrences of $J^1$ on the same atom, together with the atom to which they are attached, form a 3-6 membered non-aromatic monocyclic ring; the ring formed by two occurrences of $J^1$ on the same atom is optionally substituted with 0-3 $J^{2A}$ groups; or two occurrences of $J^1$, together with $Q^X$, form a bridged ring system;

$Q^Y$ is independently selected from a 3-7 membered monocyclic fully saturated, partially unsaturated, or aromatic ring containing 0-3 heteroatoms independently selected from nitrogen, oxygen, or sulfur; or an 8-12 membered bicyclic fully saturated, partially unsaturated, or aromatic ring containing 0-5 heteroatoms independently selected from nitrogen, oxygen, or sulfur;

$J^2$ is independently selected from halo; =O; —CN; a 3-6 membered aromatic or non-aromatic ring containing 0-3 heteroatoms selected from oxygen, nitrogen, or sulfur; or $C_{1-4}$aliphatic chain wherein up to two methylene units of the aliphatic chain are optionally replaced with —O—, —NR—, —S—, —C(O)—, S(O)—, or —S(O)$_2$—; $J^2$ is optionally substituted with 0-5 $J^3$ groups; or two occurrences of $J^2$, together with the atom or atoms to which they are attached, form a 3-6 membered aromatic or non-aromatic monocyclic ring; the ring formed by two occurrences of $J^2$ is optionally substituted with 0-3 $J^{3A}$ groups; or two occurrences of $J^2$, together with $Q^Y$, form a bridged ring system;

$J^{2A}$ is independently selected from halo or a $C_{1-4}$aliphatic chain wherein up to two methylene units of the aliphatic chain are optionally replaced with —O—, —NR—, —S—, —S(O)—, —S(O)$_2$, or —C(O);

$J^3$ and $J^{3A}$ are independently selected from halo or $C_{1-4}$alkyl; and

R is independently selected from H or $C_{1-6}$aliphatic.

2. The compound of claim 1, wherein each $R^1$ is independently a $C_{1-10}$aliphatic chain wherein up to four methylene units of the aliphatic chain are optionally replaced with —O—.

3. The compound of claim 1, wherein $Z^3$ is CH, wherein CH is optionally substituted with X.

4. The compound of claim 3, wherein each $R^1$ is independently a $C_{1-10}$aliphatic chain wherein up to four methylene units of the aliphatic chain are optionally replaced with —O—.

5. The compound of claim 4, wherein $R^1$ is independently selected from the group consisting of $C_{1-6}$alkyl, —($C_{1-4}$alkyl)O($C_{1-4}$alkyl), and alkenyl.

6. The compound of claim 1, wherein $Z^1$, $Z^2$, and $Z^3$ are independently CH, wherein CH is optionally substituted with X.

7. The compound of claim 6, wherein each $R^1$ is independently a $C_{1-10}$aliphatic chain wherein up to four methylene units of the aliphatic chain are optionally replaced with —O—.

8. The compound of claim 7, wherein each $R^1$ is independently selected from the group consisting of $C_{1-6}$alkyl, —($C_{1-4}$alkyl)O($C_{1-4}$alkyl), and alkenyl.

9. The compound of claim 1, wherein X is fluoro.

10. The compound of claim 1, wherein X is chloro.

11. A compound of formula I-B:

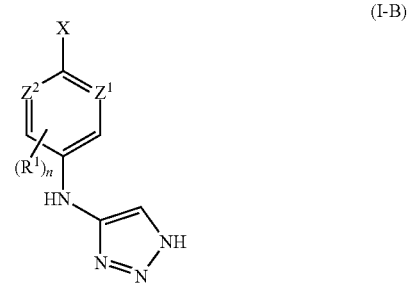

(I-B)

or a pharmaceutically acceptable salt thereof, wherein:

n is 0-4;

X is bromo or chloro; and $Z^1$ and $Z^2$ are CH, wherein CH is optionally substituted with $R^1$;

$R^1$ is independently selected from halo; —CN; $Q^X$; or a $C_{1-10}$aliphatic chain wherein up to four methylene units of the aliphatic chain are optionally replaced with —O—, —NR—, —S—, —C(O)—, S(O)—, or —S(O)$_2$—; $R^1$ is optionally substituted with 0-5 $J^1$ groups;

$Q^X$ is a 3-7 membered monocyclic fully saturated, partially unsaturated, or aromatic ring containing 0-3 heteroatoms independently selected from nitrogen, oxygen, or sulfur;

$J^1$ is independently selected from halo; —CN; $Q^Y$; or a $C_{1-6}$aliphatic chain wherein up to three methylene units of the aliphatic chain are optionally replaced with —O—, —NR—, —S—, —C(O)—, S(O)—, or —S(O)$_2$—; $J^1$ is optionally substituted with 0-5 $J^2$ groups; or two occurrences of $J^1$ on the same atom, together with the atom to which they are attached, form a 3-6 membered non-aromatic monocyclic ring; the ring formed by two occurrences of $J^1$ on the same atom is optionally substituted with 0-3 $J^{2A}$ groups; or two occurrences of $J^1$, together with $Q^X$, form a bridged ring system;

$Q^Y$ is independently selected from a 3-7 membered monocyclic fully saturated, partially unsaturated, or aromatic ring containing 0-3 heteroatoms independently selected from nitrogen, oxygen, or sulfur; or an 8-12 membered bicyclic fully saturated, partially unsaturated, or aromatic ring containing 0-5 heteroatoms independently selected from nitrogen, oxygen, or sulfur;

$J^2$ is independently selected from halo; =O; —CN; a 3-6 membered aromatic or non-aromatic ring containing 0-3 heteroatoms selected from oxygen, nitrogen, or sulfur; or $C_{1-4}$aliphatic chain wherein up to two methylene units of the aliphatic chain are optionally replaced with —O—, —NR—, —S—, —C(O)—, S(O)—, or —S(O)$_2$—; $J^2$ is optionally substituted with 0-5 $J^3$ groups; or two occurrences of $J^2$, together with the atom or atoms to which they are attached, form a 3-6 membered aromatic or non-aromatic monocyclic ring; the ring formed by two occurrences of $J^2$ is optionally substituted with 0-3 $J^{3A}$ groups; or two occurrences of $J^2$, together with $Q^Y$, form a bridged ring system;

$J^{2A}$ is independently selected from halo or a $C_{1-4}$aliphatic chain wherein up to two methylene units of the aliphatic chain are optionally replaced with —O—, —NR—, —S—, —S(O)—, —S(O)$_2$, or —C(O);

$J^3$ and $J^{3,4}$ are independently selected from halo or $C_{1-4}$alkyl; and

R is independently selected from H or $C_{1-6}$aliphatic.

12. The compound of claim 11, wherein each $R^1$ is independently a $C_{1-8}$aliphatic chain wherein up to four methylene units of the aliphatic chain are optionally replaced with —O—.

13. The compound of claim 12, wherein $R^1$ is independently selected from the group consisting of $C_{1-6}$alkyl, —($C_{1-4}$alkyl)O($C_{1-4}$alkyl), and alkenyl.

14. The compound of claim 12, wherein n is 1.

15. The compound of claim 11, wherein X is chloro.

16. The compound of claim 11, wherein n is 0.

17. The compound of claim 11, wherein X is bromo.

18. A compound of claim 11 having the structure:

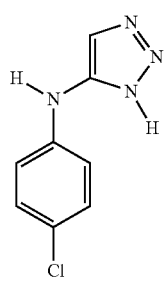 [SMILES: Clc1ccc(Nc2cnn[nH]2)cc1]

or a pharmaceutically acceptable salt thereof.

19. A pharmaceutically acceptable salt of the compound of claim 18.

20. A composition comprising a compound of claim 18, and a pharmaceutically acceptable carrier, adjuvant, or vehicle.

21. A compound selected from the group consisting of:

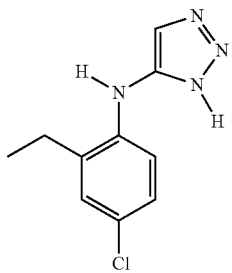
I-1

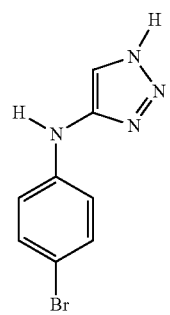
I-3

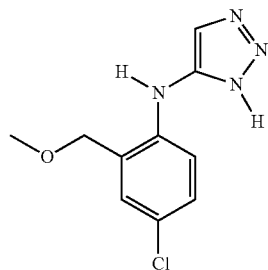
I-4

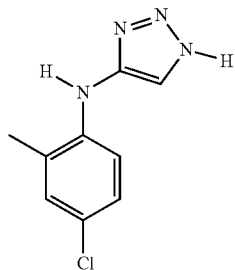
I-5

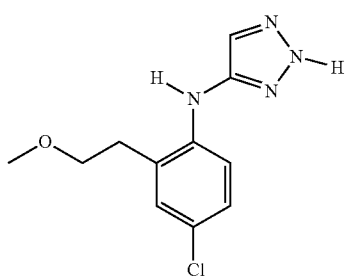
I-6

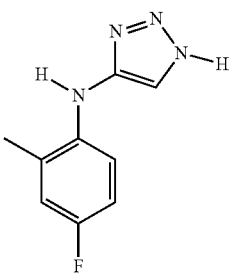
I-36

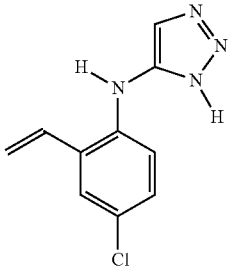
I-40

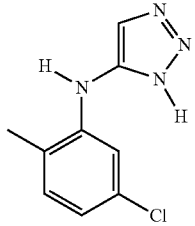
I-42 and pharmaceutically acceptable salts thereof.

22. A method of inhibiting IDO activity in a patient comprising administering to said patient
   a composition of claim 20; or
   a compound of claim 18.

23. A method of inhibiting IDO activity in a biological sample comprising contacting said biologic sample with:
   a composition of claim 20; or
   a compound of claim 18.

24. A method of treating or lessening the severity of a disease or condition of a patient selected from cancer, proliferative disorder, viral disease, sepsis, pneumonia, bacteremia, trauma, tuberculosis, parasitic disease, neuroinflammation, schizophrenia, depression, neurodegenerative disease, and pain comprising the step of administering to said patient:
   a composition of claim 20; or
   a compound of claim 18.

25. The method of claim 24, wherein the disease is cancer.

26. The method of claim 24, wherein the disease is sepsis.

27. The method according to claim 24, comprising the additional step of administering to said patient an additional therapeutic agent selected from a chemotherapeutic or antiproliferative agent, an anti-inflammatory agent, an immunomodulatory or immunosuppressive agent, a neurotrophic factor, an agent for treating cardiovascular disease, an agent for treating destructive bone disorders, an anti-viral agent, an agent for treating blood disorders, or an agent for treating immunodeficiency disorders, wherein;
   said additional therapeutic agent is appropriate for the disease being treated; and
   said additional therapeutic agent is administered together with said composition as a single dosage form or separately from said composition as part of a multiple dosage form.

28. The method of claim 27, wherein the disease is cancer.

29. The method of claim 27, wherein the disease is sepsis.

\* \* \* \* \*

UNITED STATES PATENT AND TRADEMARK OFFICE
CERTIFICATE OF CORRECTION

PATENT NO.        : 9,499,497 B2                             Page 1 of 2
APPLICATION NO.   : 14/722413
DATED             : November 22, 2016
INVENTOR(S)       : Dean Boyall et al.

It is certified that error appears in the above-identified patent and that said Letters Patent is hereby corrected as shown below:

In the Claims

| | |
|---|---|
| Claim 1, Column 62, Line 67 | Replace "or" with "and" |
| Claim 1, Column 63, Line 4 | Replace "S(O)-" with "-S(O)-" |
| Claim 1, Column 63, Line 14 | Delete "selected from" |
| Claim 1, Column 63, Line 17 | Replace "or sulfur" with "and sulfur" |
| Claim 1, Column 63, Line 20 | Replace "or" with "and" |
| Claim 1, Column 63, Line 21 | Delete "selected from" |
| Claim 1, Column 63, Line 23 | Replace "or" with "and" |
| Claim 1, Column 63, Line 27 | Replace "S(O)-" with "-S(O)-" |
| Claim 1, Column 63, Line 36 | Delete "selected from" |
| Claim 1, Column 63, Line 39 | Replace "-S(O)2" with "-S(O)2-"; Replace "-C(O)" with "-C(O)-" |
| Claim 1, Column 63, Line 40 | Delete "selected from" |
| Claim 1, Column 63, Line 42 | Delete "selected from" |
| Claim 11, Column 64, Line 21 | Delete "selected from" |
| Claim 11, Column 64, Line 24 | Replace "S(O)-" with "-S(O)-" |
| Claim 11, Column 64, Line 29 | Replace "or" with "and" |
| Claim 11, Column 64, Line 30 | Delete "selected from" |
| Claim 11, Column 64, Line 33 | Replace "S(O)-" with "-S(O)-" |
| Claim 11, Column 64, Line 43 | Delete "selected from" |
| Claim 11, Column 64, Line 46 | Replace "or sulfur" with "and sulfur" |
| Claim 11, Column 64, Line 49 | Replace "or" with "and" |
| Claim 11, Column 64, Line 50 | Delete "selected from" |
| Claim 11, Column 64, Line 52 | Replace "or" with "and" |
| Claim 11, Column 64, Line 55 | Replace "S(O)-" with "-S(O)-" |
| Claim 11, Column 64, Line 64 | Delete "selected from" |
| Claim 11, Column 64, Line 67 | Replace "-S(O)2" with "-S(O)2-"; Replace "-C(O)" with "-C(O)-" |
| Claim 11, Column 65, Line 1 | Delete "selected from" |

Signed and Sealed this
Fourth Day of April, 2017

Michelle K. Lee
*Director of the United States Patent and Trademark Office*

CERTIFICATE OF CORRECTION (continued)
U.S. Pat. No. 9,499,497 B2

Claim 11, Column 65, Line 3           Delete "selected from"
Claim 12, Column 65, Line 8           Replace "-O" with "-O-"
Claim 27, Column 68, Line 8           Replace "or" with "and"